US011406352B2

(12) United States Patent
Coolidge et al.

(10) Patent No.: US 11,406,352 B2
(45) Date of Patent: Aug. 9, 2022

(54) POSITION SENSING IN INTRAVASCULAR PROCESSES

(71) Applicant: ACIST Medical Systems, Inc., Eden Prairie, MN (US)

(72) Inventors: Troy Marshall Coolidge, Victoria, MN (US); Derek Pfeffer, Plymouth, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 379 days.

(21) Appl. No.: 15/598,991

(22) Filed: May 18, 2017

(65) Prior Publication Data
US 2017/0332999 A1    Nov. 23, 2017

Related U.S. Application Data

(60) Provisional application No. 62/338,895, filed on May 19, 2016.

(51) Int. Cl.
*A61B 8/12* (2006.01)
*A61B 8/00* (2006.01)
(Continued)

(52) U.S. Cl.
CPC .............. *A61B 8/12* (2013.01); *A61B 5/0215* (2013.01); *A61B 5/061* (2013.01);
(Continued)

(58) Field of Classification Search
CPC ....... A61B 5/061; A61B 8/4254; A61B 8/445; G01D 5/2451; A61M 25/0113; A61M 25/0105
See application file for complete search history.

(56) References Cited

U.S. PATENT DOCUMENTS

| 4,756,313 A | 7/1988 | Terwilliger |
| 5,244,461 A | 9/1993 | Derlien |

(Continued)

FOREIGN PATENT DOCUMENTS

| AU | 2013201648 B2 | 4/2014 |
| CN | 101687087 A | 3/2010 |

(Continued)

OTHER PUBLICATIONS

International Patent Application No. PCT/US2017/033331, International Search Report & Written Opinion dated Jul. 31, 2017, 13 pages.

(Continued)

*Primary Examiner* — Boniface Ngathi N
*Assistant Examiner* — Milton Truong
(74) *Attorney, Agent, or Firm* — Fredrikson & Byron, P.A.

(57) ABSTRACT

Systems can include at least one friction wheel configured to engage a catheter of an intravascular system such that proximal or distal motion of the catheter causes the friction wheel to rotate. A position sensor can include a reference element and a movable element, wherein the movable element is configured to move relative to the reference element in response to rotation of the at least one friction wheel. The position sensor can provide a position signal representative of the rotation of the at least one friction wheel. An intravascular processing engine can receive both the position signal from the position sensor and an intravascular signal from the catheter.

18 Claims, 10 Drawing Sheets

(51) Int. Cl.
*A61B 8/08* (2006.01)
*A61B 8/06* (2006.01)
*A61B 5/0215* (2006.01)
*A61B 5/06* (2006.01)
*A61B 5/145* (2006.01)
*G01S 15/89* (2006.01)

(52) U.S. Cl.
CPC ............ *A61B 5/14503* (2013.01); *A61B 8/06* (2013.01); *A61B 8/085* (2013.01); *A61B 8/0891* (2013.01); *A61B 8/4254* (2013.01); *A61B 8/445* (2013.01); *A61B 8/483* (2013.01); *A61B 8/5207* (2013.01); *G01S 15/899* (2013.01); *A61B 8/44* (2013.01); *G01S 15/89* (2013.01)

(56) References Cited

U.S. PATENT DOCUMENTS

| | | | |
|---|---|---|---|
| 5,327,885 | A | 7/1994 | Griffith |
| 5,361,768 | A | 11/1994 | Webler et al. |
| 5,827,313 | A | 10/1998 | Ream et al. |
| 5,908,395 | A | 6/1999 | Stalker et al. |
| 6,004,269 | A | 12/1999 | Crowley et al. |
| 6,004,271 | A | 12/1999 | Moore et al. |
| 6,035,229 | A | 3/2000 | Silverstein et al. |
| 6,226,546 | B1 | 5/2001 | Evans |
| 6,251,078 | B1 | 6/2001 | Moore et al. |
| 6,263,230 | B1 | 7/2001 | Haynor |
| 6,292,681 | B1 | 9/2001 | Moore |
| 6,319,227 | B1 | 11/2001 | Mansouri-Ruiz |
| 6,321,106 | B1 | 11/2001 | Lemelson |
| 6,398,755 | B1 | 6/2002 | Belef et al. |
| 6,511,432 | B2 | 1/2003 | Moore et al. |
| 6,592,520 | B1 | 7/2003 | Peszynski et al. |
| 6,974,465 | B2 | 12/2005 | Belef et al. |
| 8,157,741 | B2 | 4/2012 | Hirota |
| 8,298,156 | B2 | 10/2012 | Manstrom et al. |
| 9,138,248 | B2 | 9/2015 | Sliwa et al. |
| 9,492,638 | B2 | 11/2016 | McKinnis et al. |
| 2001/0021841 | A1 | 9/2001 | Webler et al. |
| 2001/0045935 | A1 | 11/2001 | Chang et al. |
| 2001/0047165 | A1 | 11/2001 | Makower et al. |
| 2002/0047367 | A1 | 4/2002 | Kim et al. |
| 2002/0050169 | A1 | 5/2002 | Ritter et al. |
| 2002/0093880 | A1 | 7/2002 | Nakamura |
| 2002/0107447 | A1 | 8/2002 | Suorsa et al. |
| 2002/0183723 | A1 | 12/2002 | Belef et al. |
| 2003/0013958 | A1 | 1/2003 | Govari et al. |
| 2003/0069719 | A1* | 4/2003 | Cunningham ......... G09B 23/30 703/7 |
| 2003/0135995 | A1 | 7/2003 | Glasson |
| 2003/0171678 | A1 | 9/2003 | Batten et al. |
| 2003/0187369 | A1 | 10/2003 | Lewis et al. |
| 2004/0078036 | A1 | 4/2004 | Keidar |
| 2004/0097803 | A1 | 5/2004 | Panescu |
| 2004/0133105 | A1 | 7/2004 | Ostrovsky et al. |
| 2004/0147920 | A1 | 7/2004 | Keidar |
| 2004/0215130 | A1 | 10/2004 | Rioux et al. |
| 2005/0054929 | A1 | 3/2005 | Angelsen et al. |
| 2006/0031953 | A1 | 2/2006 | Cheah |
| 2006/0106375 | A1 | 5/2006 | Werneth et al. |
| 2006/0122514 | A1 | 6/2006 | Byrd et al. |
| 2006/0224153 | A1 | 10/2006 | Fischell et al. |
| 2006/0241445 | A1 | 10/2006 | Altmann et al. |
| 2006/0241469 | A1 | 10/2006 | Rold et al. |
| 2006/0241484 | A1 | 10/2006 | Horiike et al. |
| 2006/0287599 | A1 | 12/2006 | Cimino |
| 2007/0014445 | A1 | 1/2007 | Lin |
| 2007/0066890 | A1 | 3/2007 | Maschke |
| 2007/0093752 | A1 | 4/2007 | Zhao et al. |
| 2007/0106147 | A1 | 5/2007 | Altmann et al. |
| 2007/0135803 | A1* | 6/2007 | Belson ................... A61B 5/064 606/1 |
| 2007/0167752 | A1 | 7/2007 | Proulx et al. |
| 2007/0167821 | A1 | 7/2007 | Lee et al. |
| 2008/0146941 | A1 | 6/2008 | Dala-Krishna |
| 2008/0154131 | A1 | 6/2008 | Lee et al. |
| 2008/0177180 | A1 | 7/2008 | Azhari et al. |
| 2008/0195041 | A1 | 8/2008 | Goldfarb et al. |
| 2008/0200801 | A1 | 8/2008 | Wildes et al. |
| 2008/0255449 | A1 | 10/2008 | Warnking et al. |
| 2008/0255475 | A1 | 10/2008 | Kondrosky |
| 2009/0054776 | A1 | 2/2009 | Sasaki |
| 2009/0069693 | A1 | 3/2009 | Burcher et al. |
| 2009/0088628 | A1 | 4/2009 | Klingenbeck-Regn |
| 2009/0124998 | A1 | 5/2009 | Rioux et al. |
| 2009/0137952 | A1 | 5/2009 | Ramamurthy et al. |
| 2009/0156941 | A1 | 6/2009 | Moore |
| 2009/0234220 | A1 | 9/2009 | Maschke |
| 2009/0234302 | A1 | 9/2009 | Hoendervoogt et al. |
| 2009/0234445 | A1 | 9/2009 | Maschke |
| 2010/0016710 | A1 | 1/2010 | Kumar et al. |
| 2010/0057019 | A1 | 3/2010 | Zelenka |
| 2010/0152590 | A1 | 6/2010 | Moore et al. |
| 2010/0179434 | A1 | 7/2010 | Thornton |
| 2010/0249603 | A1 | 9/2010 | Hastings et al. |
| 2011/0021924 | A1 | 1/2011 | Sethuraman et al. |
| 2011/0178508 | A1* | 7/2011 | Ullrich ................... A61B 34/70 606/1 |
| 2011/0184406 | A1 | 7/2011 | Selkee |
| 2011/0230906 | A1 | 9/2011 | Modesitt |
| 2012/0071752 | A1 | 3/2012 | Sewell et al. |
| 2012/0150035 | A1 | 6/2012 | Seip et al. |
| 2013/0039294 | A1 | 2/2013 | Wang |
| 2013/0137963 | A1 | 5/2013 | Olson |
| 2013/0172713 | A1 | 7/2013 | Kirschenman |
| 2013/0211436 | A1 | 8/2013 | Larson et al. |
| 2013/0274657 | A1* | 10/2013 | Zirps ................... A61M 25/0113 604/95.01 |
| 2014/0039294 | A1 | 2/2014 | Jiang |
| 2014/0163361 | A1 | 6/2014 | Stigall et al. |
| 2014/0180127 | A1 | 6/2014 | Meyer et al. |
| 2014/0343433 | A1* | 11/2014 | Elbert ................... A61B 8/54 600/467 |
| 2015/0038824 | A1 | 2/2015 | Lupotti |
| 2015/0065956 | A1 | 3/2015 | Huang |
| 2015/0182190 | A1 | 7/2015 | Hiltner et al. |
| 2015/0297864 | A1* | 10/2015 | Kokish ................... A61B 34/30 604/95.04 |
| 2016/0081657 | A1* | 3/2016 | Rice ....................... A61B 8/445 600/301 |
| 2016/0220314 | A1 | 8/2016 | Huelman |
| 2017/0333000 | A1 | 11/2017 | Nystrom et al. |

FOREIGN PATENT DOCUMENTS

| | | |
|---|---|---|
| CN | 103037759 A | 4/2013 |
| CN | 103037761 A | 4/2013 |
| CN | 202876024 U | 4/2013 |
| CN | 103385706 A | 11/2013 |
| CN | 103635146 A | 3/2014 |
| CN | 105025787 A | 11/2015 |
| EP | 1929954 A1 | 6/2008 |
| EP | 1952768 A2 | 8/2008 |
| EP | 2358278 A2 | 8/2011 |
| EP | 2749240 A2 | 7/2014 |
| JP | S63122923 A | 5/1988 |
| JP | S63281632 A | 11/1988 |
| JP | S63302836 A | 12/1988 |
| JP | H0417843 A | 1/1992 |
| JP | H05244694 A | 9/1993 |
| JP | H078497 A | 1/1995 |
| JP | H0795980 A | 4/1995 |
| JP | H07136171 A | 5/1995 |
| JP | H07184902 A | 7/1995 |
| JP | H07508204 A | 9/1995 |
| JP | H08112286 A | 5/1996 |
| JP | 2000157546 A | 6/2000 |
| JP | 2000271124 A | 10/2000 |
| JP | 2002301070 A | 10/2002 |
| JP | 2003265483 A | 9/2003 |

(56) References Cited

FOREIGN PATENT DOCUMENTS

| | | |
|---|---|---|
| JP | 2004209277 A | 7/2004 |
| JP | 2005507273 A | 3/2005 |
| JP | 2005536289 A | 12/2005 |
| JP | 2006102240 A | 4/2006 |
| JP | 2007044074 A | 2/2007 |
| JP | 2007105450 A | 4/2007 |
| JP | 2007152094 A | 6/2007 |
| JP | 2007268132 A | 10/2007 |
| JP | 2008053887 A | 3/2008 |
| JP | 2008155022 A | 7/2008 |
| JP | 2008178676 A | 8/2008 |
| JP | 2008277834 A | 11/2008 |
| JP | 2008539887 A | 11/2008 |
| JP | 2011519678 A | 7/2011 |
| JP | 2012510885 A | 5/2012 |
| JP | 2015520641 A | 7/2015 |
| WO | 9203095 A1 | 3/1992 |
| WO | 2003011139 A1 | 2/2003 |
| WO | 2007044792 A1 | 4/2007 |
| WO | 2008042423 A2 | 4/2008 |
| WO | 2008086613 A1 | 7/2008 |
| WO | 2010077632 A2 | 7/2010 |
| WO | 2010107916 A1 | 9/2010 |
| WO | 2011058493 A1 | 5/2011 |
| WO | 2015073817 A1 | 5/2015 |
| WO | 2015102573 A1 | 7/2015 |

OTHER PUBLICATIONS

Casaclang-Verzosa, G. et al., "Structural and functional remodeling of the left atrium," Journal of American College of Cardiology, vol. 51, No. 1, Jan. 2008, 11 pgs.

Baello, et al., "Ultrasound Study of Acoustic Properties of the Normal Canine Heart: Comparison of Backscatter From all Chambers," JACC vol. 8, No. 4, Oct. 1985:880-4.

\* cited by examiner

POSITION SENSING IN INTRAVASCULAR PROCESSES

PRIORITY CLAIM

This application claims priority to U.S. provisional patent application No. 62/338,895 filed May 19, 2016.

TECHNICAL FIELD

This disclosure relates to an intravascular system and a method of operating the same.

BACKGROUND

Intravascular processes such as imaging processes or receiving other physiological measurements (e.g., measurements of blood parameters, such as blood pressure, oxygen saturation levels, blood pH, etc.) are often used to identify diagnostically significant characteristics of a vessel. For example, an intravascular imaging system may be used by a healthcare professional to help identify and locate blockages or lesions in a vessel. Common intravascular imaging systems include intravascular ultrasound (IVUS) systems as well as optical coherence tomography (OCT) systems.

Intravascular imaging involves one or more transducers emitting and/or receiving energy based on received electrical signals and sending return electrical signals based on signals reflected by various intravascular structures. Intravascular imaging is often used to generate images. In some instances, a console with a high-resolution display is able to display intravascular images in real-time. In this way, intravascular imaging can be used to provide in-vivo visualization of the vascular structures and lumens, including the coronary artery lumen, coronary artery wall morphology, and devices, such as stents, at or near the surface of the coronary artery wall. Intravascular imaging may be used to visualize diseased vessels, including coronary artery disease. In some instances, the transducer(s) can be carried near a distal end of an intravascular imaging catheter. Some intravascular imaging systems involve rotating the intravascular imaging catheter (e.g., mechanically, phased-array, etc.) for 360-degree visualization.

Many intravascular imaging systems are configured to perform translation operations, in which imaging components of the catheter are translated through a patient's blood vessel while acquiring images. The result is a 360-degree image with a longitudinal component. When performing a translation operation, it can be important to accurately determine at least the relative amount of translation of the catheter's imaging components in order to accurately construct the 360-degree image.

In other intravascular processes, intravascular blood pressure measurements may be used for evaluating the degree to which a stenotic lesion obstructs flow through a blood vessel, such as a Fractional Flow Reserve measurement (FFR). To calculate the FFR for a given stenosis, two blood pressure readings are taken using a pressure sensor, such as a monorail pressure sensor (MPS). One pressure reading is taken on the distal side of the stenosis (e.g., downstream from the stenosis), the other pressure reading is taken on the proximal side of the stenosis (e.g., upstream from the stenosis, towards the aorta). The FFR is defined as the ratio of maximal blood flow in a stenotic artery, taken distal to the lesion, to normal maximal flow, and is typically calculated based on a measured pressure gradient of the distal pressure to the proximal pressure. The FFR is therefore a unitless ratio of the distal and proximal pressures. The pressure gradient, or pressure drop, across a stenotic lesion is an indicator of the severity of the stenosis, and the FFR is a useful tool in assessing the pressure drop. The more restrictive the stenosis is, the greater the pressure drop, and the lower the resulting FFR. The FFR measurement may be a useful diagnostic tool.

One method of measuring the pressure gradient across a lesion is to use a small catheter connected to a blood pressure measurement sensor. The catheter would be passed over the guidewire which has already been placed across the lesion. The catheter would be advanced down the guidewire until the tip of the catheter crosses the lesion. The blood pressure on the distal side of the lesion is recorded. This pressure would be divided by the pressure value recorded in the aorta. A disadvantage of using this method is that some error may be introduced due to the cross sectional size of the catheter. As the catheter crosses the lesion, the catheter itself introduces blockage, in addition to that caused by the lesion itself. The measured distal pressure would therefore be somewhat lower than it would be without the additional flow obstruction, which may exaggerate the measured pressure gradient across the lesion.

Pressure drop can also be measured across a heart valve. When a heart valve is regurgitant, a less than optimal pressure drop is typically observed. Using a catheter to measure pressure drop is common across a heart valve. However, because of the catheter size, the heart valve may not seal well around the catheter. Leakage might also result from the presence of the catheter and may contribute to an inaccurate pressure drop reading. One example of where this could occur is in the mitral valve (e.g., mitral valve regurgitation).

One method of measuring blood pressure in a patient is to use a pressure sensing guidewire. Such a device has a pressure sensor embedded within the guidewire itself. A pressure sensing guidewire can be used in the deployment of interventional devices such as angioplasty balloons or stents. Prior to the intervention, the pressure sensing guidewire would be deployed across a stenotic lesion so the sensing element is on the distal side of the lesion and the distal blood pressure is recorded. The guidewire may then be retracted so the sensing element is on the proximal side of the lesion. The pressure gradient across the stenosis and the resulting FFR value can then be calculated.

To use a guidewire-based pressure sensor in certain applications, the guidewire must be repositioned so the sensing element of the guidewire is correctly placed with respect to a stenotic lesion, for example. Blood pressure measurements for calculating FFR, for example, are generally taken on both sides of a given stenosis, so the guidewire is typically retracted across the stenosis to make the upstream measurement. After retracting the guidewire to make the proximal pressure measurement (aortic pressure or upstream coronary pressure), the guidewire may again be repositioned downstream of the lesion, for example, if it is determined (e.g., based on the FFR calculation) that an interventional device should be deployed. In cases where there are multiple lesions, the sensing element of a pressure sensing guidewire would need to be advanced and retracted across multiple lesions, and would potentially have to be advanced and repositioned again for each such lesion. Advancing and maneuvering a pressure sensing guidewire though stenotic lesions and the vasculature, for example, can be a difficult and/or time consuming task.

In existing systems, the amount of translation or maneuvering of intravascular catheter components is often estimated by attempting to translate portions of the catheter at a certain velocity for a certain amount of time. If the catheter's components are translated at a certain velocity for a certain time, the translated distance can be calculated. However, if the actual translation velocity is not the same as the commanded velocity, for example, or cannot be otherwise reliably measured or produced, inaccuracies in determining the amount of translation can occur. Inaccurate translation determinations can lead to errors in determining position-dependent information of the patient's vasculature. Additionally or alternatively, in some procedures, it may not be necessary or even desirable to pull the catheter back at a fixed velocity. For example, an operator may want to spend more time analyzing areas of interest, or to return to an area of interest by navigating the catheter in the opposite direction. In still further examples, velocity is not measured, and distances may simply be estimated by a system operator. Accordingly, more reliable position sensing mechanism may be useful in performing position-sensitive intravascular processes.

SUMMARY

Aspects of this disclosure include systems and methods for monitoring the position of one or more components of a catheter. Some exemplary systems include a catheter having a proximal end, a distal end, a sensor located at the distal end, and a cable extending from the proximal end of the catheter to the distal end of the catheter. The cable can be operatively connected to the sensor at the distal end, and the sensor can be configured to provide an intravascular signal representative of one or more intravascular properties of a patient. Exemplary sensors can include ultrasound transducers, pressure sensors, or the like.

Exemplary systems can include at least one friction wheel operatively engaging the cable of the catheter. The engagement between the at least one friction wheel and the cable can be such that distal and proximal motion of the cable causes rotation of the at least one friction wheel. In some examples, systems can include a first friction wheel and a second friction wheel positioned generally opposite one another such that the cable of the catheter extends between the first and second friction wheels. In some such examples at least one of the first and second friction wheels can be spring-biased against the catheter cable.

Systems can include a position sensor. Exemplary position sensors can include a reference element and a movable element, and can be configured to generate a position signal based on the relationship between the reference element and the movable element. In some embodiments, the movable element is configured to move relative to the reference element in response to rotation of at least one friction wheel.

Systems can include an intravascular processing engine in communication with the catheter sensor and the position sensor. The intravascular processing engine can be configured to receive the intravascular signal from the sensor of the catheter and also the position signal from the position sensor. In some examples, the received data in the intravascular signal can be associated with the positions in received position signal.

Aspects of the disclosure further include position sensing systems for an intravascular system. Such systems can include at least one friction wheel and a spring mechanism biased to press at least one friction wheel against a cable of the intravascular system. Exemplary sensing systems can include at least one detectable area disposed on at least one friction wheel and a detector configured to detect relative movement of the detectable area. In some embodiments, a position sensing assembly includes a housing configured to interface with a catheter, such as the catheter of an intravascular system. For instance in some examples, a position sensing assembly housing includes a groove configured to receive an anchor portion of a catheter.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

The following detailed description should be read with reference to the accompanying drawings, in which like numerals denote like elements. The drawings, which are not necessarily to scale, depict selected embodiments of the invention—other possible embodiments may become readily apparent to those of ordinary skill in the art with the benefit of these teachings. Thus, the embodiments shown in the accompanying drawings and described below are provided for illustrative purposes, and are not intended to limit the scope of the invention as defined in the claims appended hereto.

Embodiments of the invention are generally directed toward position sensing in intravascular processes such as intravascular ultrasound (IVUS) imaging and other parameter sensing applications, for examples, using a monorail pressure sensor (MPS). Such processes typically involve inserting a catheter into the vasculature of a patient for performing at diagnostic and/or therapeutic procedures. Often it is advantageous for a medical practitioner to know at least relative positions of diagnostic or therapeutic elements attached to the catheter within the patient. For example, a diagnostic procedure such as determining pressure gradient across a stenotic lesion may lead to a medical practitioner recommending one or more treatments to be performed based on the diagnostic procedure. In some such examples, the recommended treatment is region-specific, such as placing a stent within the patient's vasculature proximate the region of the measured pressure gradient. In another example, such as in an IVUS system, a series of ultrasound measurements associated with a length of a patient's vasculature may be performed. In such examples, it can be advantageous to know at least the relative positions along the blood vessel with which various image data are associated. Thus, in many situations, it may be advantageous to know at least relative positions associated with measurements and treatments performed intravascularly.

Figure 1:
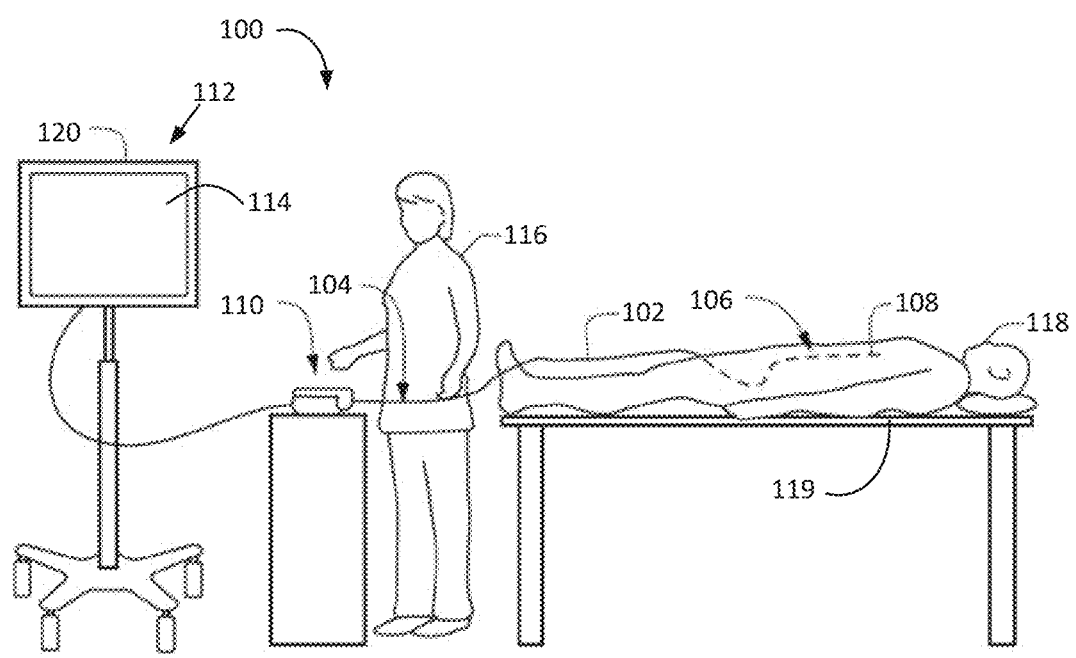
FIG. 1 is an illustrative intravascular system.

FIG. 1 is an illustrative example of a system 100 that may be configured to perform an intravascular procedure. System 100 may include a catheter 102, an interface element 110, and a processing engine 112. The catheter 102 may include a proximal end 104 and a distal end 106 configured to be inserted into a vessel of a patient 118. As shown, patient 118 is positioned on an operating table, which may comprise a surgical mat 119. In one example, catheter 102 may be inserted into the patient 118 via the femoral artery and guided to an area of interest within the patient 118. The broken lines in FIG. 1 represent portions of catheter 102 within the patient 118.

In some examples, catheter 102 may include a sensor 108 at the distal end 106 that is configured to provide information indicative of an environment within the patient's vasculature. For example, where system 100 is an IVUS system, sensor 108 may comprise an ultrasound transducer configured to emit and receive ultrasound energy and generate ultrasound data. In another imaging example, system 100 may be an OCT system, and sensor 108 may comprise an OCT transducer configured to emit and receive light and generate OCT data. The catheter 102 can be configured to generate image information and transmit that image information in an imaging procedure. In still further examples, sensor 108 may include a pressure transducer for providing a signal representative of patient blood pressure, for example.

Returning to FIG. 1, the interface element 110 of the intravascular imaging system 100 can be engaged with the catheter 102 and can provide an interface with the catheter 102, such as an electrical interface, a mechanical interface, or both. In some embodiments, the interface element 110 may include a translation mechanism configured to translate at least a portion of the catheter 102 a controlled distance within the patient 118 during a pullback or other translation operation. For example, in some embodiments, the catheter 102 comprises a drive cable or guidewire attached to the sensor 108 housed within a sheath. In some such configurations, the interface element 110 can act to translate or otherwise facilitate the translation of the drive cable and sensor 108 through the sheath while keeping the sheath substantially fixed in place.

In some examples, the processing engine 112 may be in communication with one or both of the sensor 108 and the interface element 110. For instance, in some examples, the interface element 110 is in communication with the processing engine 112 and provides an electromechanical interface to catheter 102. In some such examples, the interface element 110 facilitates communication between the processing engine 112 and the catheter 102 or elements thereof (e.g., sensor 108).

According to some examples, the processing engine 112 may comprise at least one programmable processor. In some examples, the processing engine 112 may comprise a computing machine including one or more processors configured to receive commands from a system user 116 and/or display data acquired from catheter 102 via a user interface 120. The computing machine may include computer peripherals (e.g., keyboard, mouse, electronic display) to receive inputs from the system user 116 and output system information and/or signals received from catheter 102 (e.g., rendered images, data curves, etc.). The user interface 120 may include a traditional PC or PC interface with software configured to communicate with the other components of the intravascular imaging system 100. In some embodiments, the user interface 120 may include a display 114 configured to display system information and/or representations of signals from the catheter 102 (e.g., intravascular images, pressure curves, etc.). In some embodiments, the user interface 120 includes a touchscreen display, which can act to both receive commands from a system user 116 and display intravascular imaging data from the catheter 102. In some examples, processing engine 112 may include memory modules for storing instructions, or software, executable by the one or more processors.

Figure 2:
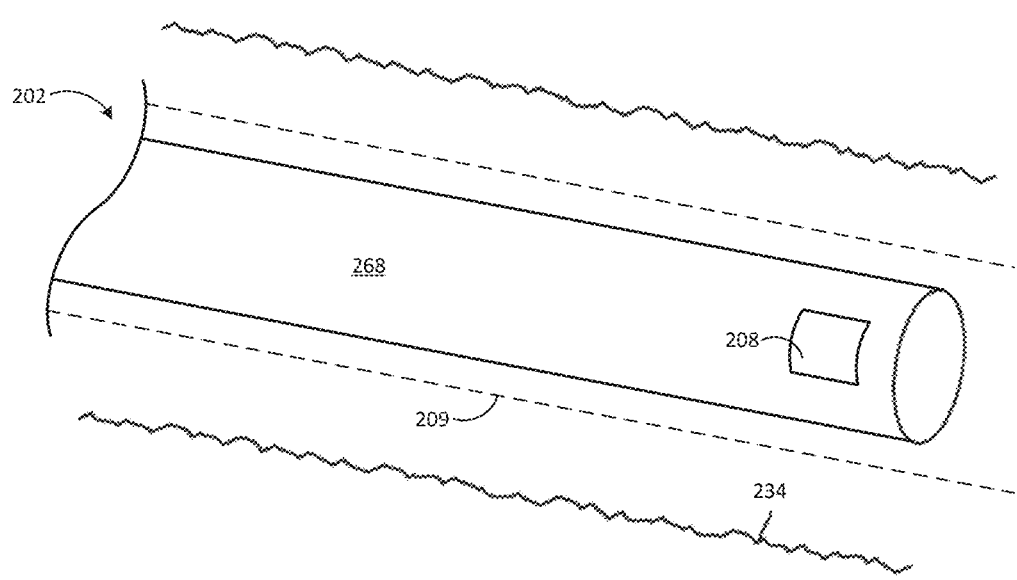
FIG. 2 is a diagram of the distal end of an exemplary catheter used in an exemplary IVUS system.

FIG. 2 is a diagram of the distal end of an exemplary catheter used in an IVUS system. The catheter 202 of FIG. 2 may be similar to catheter 102 described above. In the illustrated embodiment, catheter 202 comprises an IVUS catheter. The IVUS catheter 202 includes a sensor 208 such as a transducer configured to emit and receive ultrasonic pulses to generate a signal indicative of the interior structure of a patient's blood vessel 234. In some examples, sensor 208 may include a single transducer element or an array of transducer elements configured to emit and receive ultrasonic pulses. As shown, sensor 208 is coupled to drive cable 268, which may rotate and/or move the transducer distally or proximally within the patient's blood vessel 234. In some examples, the catheter 202 includes a sheath 209, which may remain stationary within the patient's blood vessel 234 while the drive cable 268 moves the sensor 208 distally or proximally within the sheath 209 and blood vessel 234.

Figure 3:
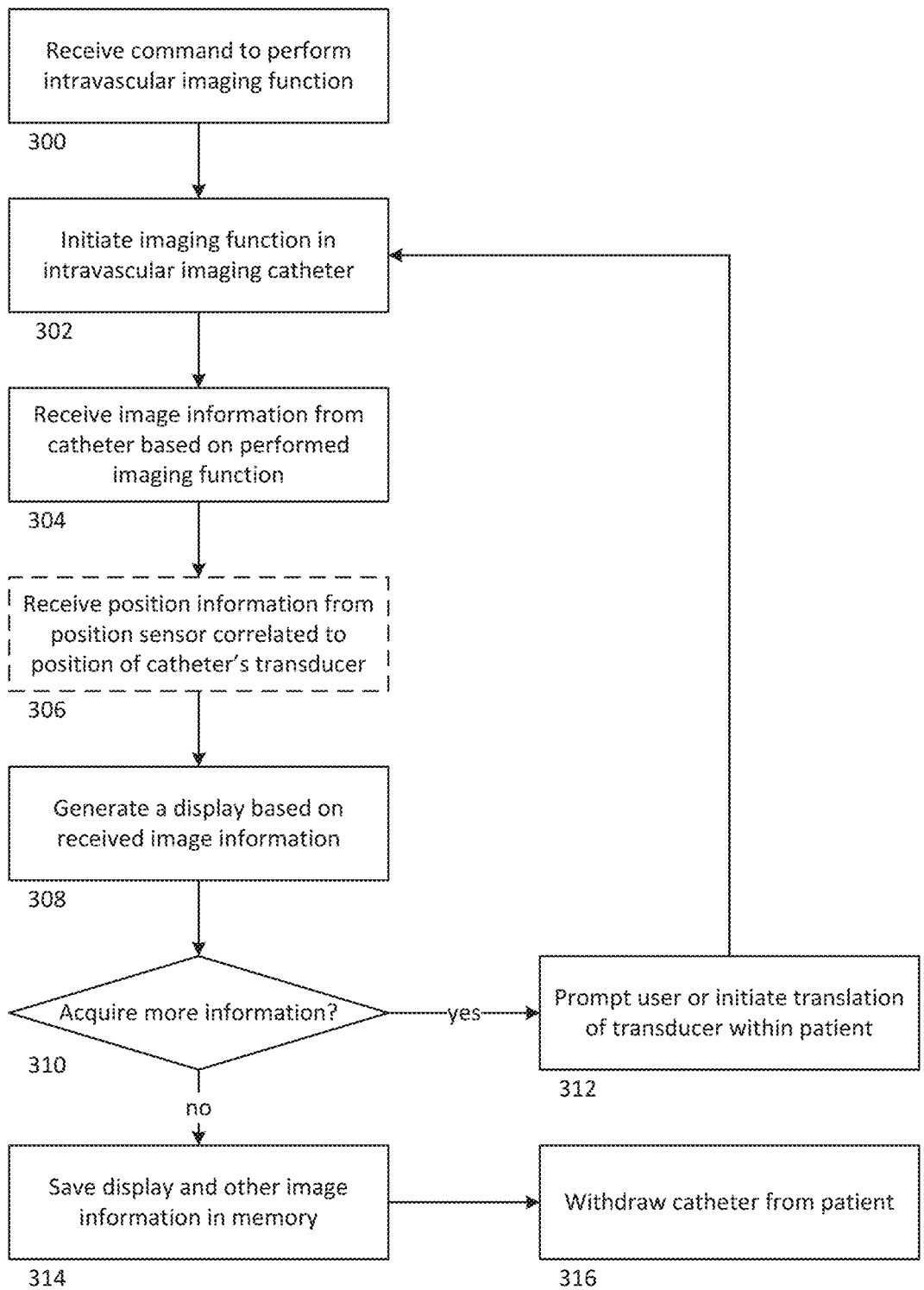
FIG. 3 is a step-flow diagram outlining a method in which one or more IVUS displays can be generated.

FIG. 3 is a step-flow diagram outlining a method in which one or more IVUS displays can be generated. After the catheter is inserted into a patient by a system operator, an intravascular processing engine such as those described herein can receive a command to perform an intravascular imaging function in step 300. The command can include parameters and scheduling of the imaging function. A user may command the processing engine to perform the imaging function. The user can manually program the desired parameters for the imaging function.

In step 302, the processing engine can initiate an imaging function commanded in the intravascular imaging catheter. This can include interfacing with the catheter, sending control signals and/or power to the catheter, rotating the catheter and/or the transducer within the catheter, or any other initiation process for performing the imaging function. In some embodiments, any single or combination of initiation processes can be initiated manually via a user interface. For example, initiating the imaging function may include directing electrical signals to the transducer resulting in the emitting of ultrasonic signals from the IVUS transducer.

After initiating an imaging function (e.g., step 302), in step 304, the processing engine can receive image information from the catheter based on the performed imaging function. The image information can be in the form of electrical or other signals from the catheter and/or transducer. In step 308, the processing engine can generate a display based on the received information. The display can be presented on a display where it can be viewed by a system user. The generated display can include, for example, a longitudinal image comprising image information from a plurality of locations within the patient and/or a cross-sectional image corresponding to a single transducer location within a patient. In some systems, the generated display can be generated by the processing engine in real-time and shown on the display as a live image. In some embodiments, the generated display can comprise a single snapshot of a cross section of a patient's vasculature triggered by a user, in which image information is captured for a single transducer location at a single time. In some embodiments, various generated displays are possible. In some systems, a user can select which mode of display is used (e.g., real-time, snapshot, etc.).

In step 310, the processing engine, based on received commands (e.g., step 300) and memory, can determine if more information is to be acquired. In some embodiments, the user can decide whether more information will be acquired. If so, the processing engine can initiate translation of the transducer within the patient, as in step 312. For example, in some systems, a selected mode of display, such as real-time display or a snap-shot display, can be used in step 310 to determine if more information is to be acquired.

In some embodiments, the intravascular imaging system comprises a translation mechanism. The translation mechanism can be configured for automated translation via a motor and/or manual operation. In some such embodiments, in step 312, the processing engine can interface with the translation mechanism and initiate translation directly via the motor. Some embodiments of the intravascular imaging system are configured for manual translation of the transducer. In such embodiments, the processing engine can prompt the user to translate the transducer.

After the transducer has been translated, step 302 may be repeated and an imaging function can again be initiated. The process may be repeated so that additional image information may be acquired at a different position within the patient. Once it is determined in step 310 that no additional information is to be acquired, the generated display or other associated image information can be saved in memory in step 314. In some embodiments, the user can manually save information to memory. Additionally or alternatively, the system may automatically save one or more pieces of information associated with system operation. If all operations utilizing the catheter are complete, in various embodiments the catheter can be withdrawn from the patient either manually or automatically in step 316.

As described, in some examples, the transducer is moved within the patient for acquisition of image data from a plurality of positions within the patient. In some embodiments, the transducer may be repositioned manually, or with the assistance of a translation mechanism. In some example, such a translation mechanism may assist a user in manually moving the transducer in any one of a desired distance, in a desired direction, and at a desired speed. Additionally or alternatively, a translation mechanism may include a motor capable of driving moving the transducer within the patient. The motor may be controlled manually or automatically, such as according to program instructions from the processing engine. Exemplary translation mechanisms are described further in U.S. patent application Ser. No. 13/894,045, filed May 14, 2013, and entitled "System and method for monitoring device engagement," which is assigned to assignee of the present application and is hereby incorporated by reference herein in its entirety.

In some embodiments in which the transducer is moved to a different position for the acquisition of additional image information, the processing engine can additionally receive position information from a position sensor as in step 306. Position information may be displayed and/or saved to memory with associated image information. In various examples, receiving image information such as in step 304 and receiving position information such as in step 306 can involve receiving any number of sets of image and position information from any number of distinct positions of the movable element of the position sensor. In some embodiments, receiving image information such as in step 304 and receiving position information such as in step 306 can include receiving a first set of image and position information corresponding to a first position of the transducer and a second set of image and position information corresponding to a second position of the transducer, such that the first and second positions are distinct from one another.

In some examples, the position information can be generated by a position sensor. Exemplary position information may comprise information regarding the relative position of a reference element of a position sensor and a movable element of the position sensor. In some configurations, the position of one of the reference and movable elements of the position sensor corresponds to the position of the transducer. Thus, relative motion of elements of the position sensor which can correspond to the relative motion of the transducer within the patient.

Because, in some embodiments, the position of the movable element of the position sensor is correlated to the position of the transducer in the patient's vasculature, the received sets of image and position information can correspond to distinct locations of the transducer. In some embodiments, at any one of the movable element positions for which the image and position information are received, the image and position information can be associated with one another as having been received at a common transducer position. Each set of image information can correspond to image information generated from a unique location within the patient's vasculature. The sets of position information can provide details on the spatial relationships between the unique locations. This can allow for the combination of image and position information from multiple movable element positions and the construction of a combined image.

In some embodiments, image and position information are received from a series of transducer positions by way of performing a pullback operation (e.g., all the way across a region of interest in a patient's blood vessel). Pullback can comprise inserting a catheter into a patient's vasculature and performing an imaging function while retracting the transducer through the patient, thereby acquiring image and position information corresponding to a plurality of transducer positions. Pullback can be executed by a motor, and can be initiated by a user via the user interface of the intravascular processing engine. A predetermined pullback operation can be performed, wherein the motor pulls the transducer back in a predetermined manner. In some embodiments, a user can manually control the operation of the motor and control the pullback operation. Motor controlled pullback can be automatically performed as part of an imaging schedule stored in memory. Automated pullback can include a feedback element configured to provide position information from the position sensor to the intravascular processing engine, and the intravascular processing engine can control the motor based on the position information. In some configurations, pullback can be performed entirely manually, in which a user manually translates the transducer within the patient while performing an imaging function. The execution of a pullback imaging operation can result in a plurality of sets of position and corresponding image information in which the relative spatial relationship between the sets of position information is known.

Image and position information from multiple movable element locations (associated with multiple transducer locations) can be combined to produce a three-dimensional volume of image information. When the relative transducer locations for each set of position and image information received are known, each set of image information can be arranged in a correct sequence and with appropriate spatial separation. In some embodiments, a single set of image data received by the intravascular processing engine comprises a cross-sectional image of the patient's vasculature proximate the transducer. A single set of position information can include a relative longitudinal location of the transducer within the patient's vasculature. A second set of image and position information received from a second position can comprise a second cross-sectional image, and the relative longitudinal location of the transducer when the image was taken. The relative relationship between the first and second transducer location can be determined by the first and second set of position information. Accordingly, the first and second set of image information can represent cross-sectional images taken at longitudinal locations a known distance apart. The cross sections can be combined along a longitudinal axis and appropriately spaced to form a three-dimensional representation of the two sets of information.

Figure 4:
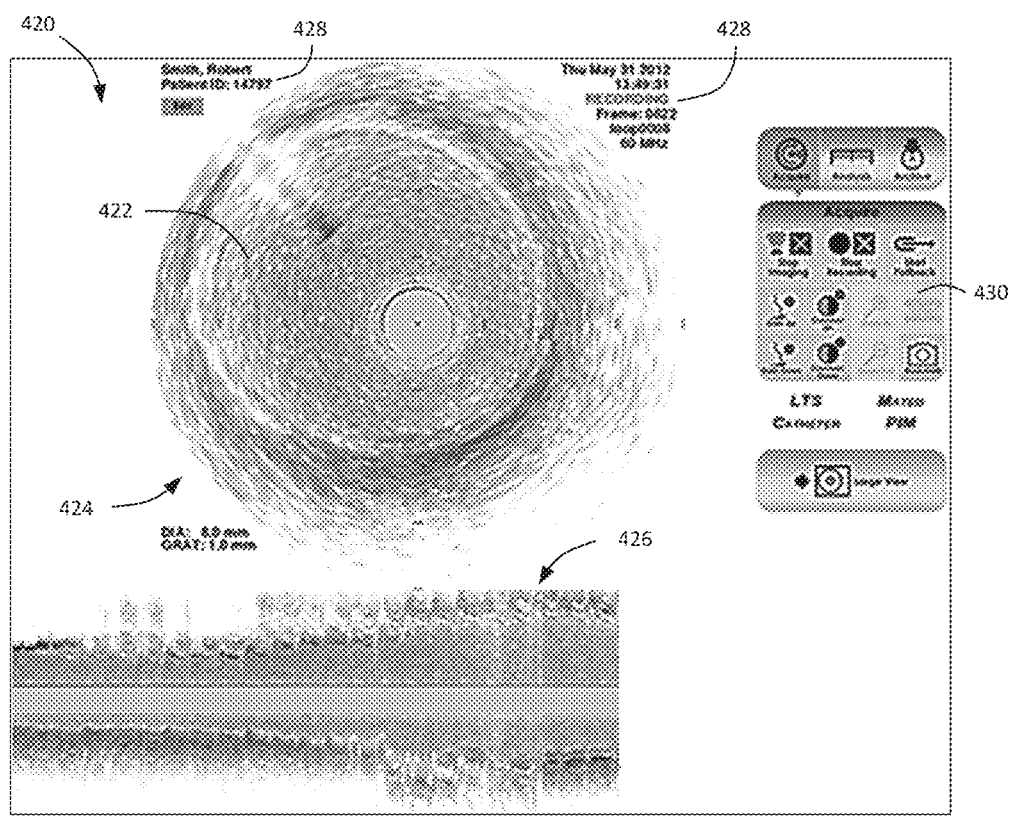
FIG. 4 shows an exemplary longitudinal image as can be constructed by an embodiment of an intravascular imaging system.

In general, any number of sets of image and position information (i.e., unique cross-sections) can be combined in this way to build up a three dimensional representation of the surroundings of the transducer, such as a patient's vasculature. Such a representation can be referred to as a longitudinal image. FIG. 4 shows an exemplary longitudinal image as can be constructed by an embodiment of an intravascular imaging system. FIG. 4 shows a display 420 such as might be shown on the display 114 of FIG. 1, for example. Referring again to FIG. 4, display 420 can include a cross-sectional image 424 configured to display a set of image information 422 corresponding to a particular transducer location. The display 420 can include a longitudinal image 426 configured to show a longitudinally arranges series of sets of image information, each from a particular transducer (e.g., sensor 108) location and arranged according to the associated position information. A longitudinal image 426 can be such that the longitudinal axis represents the direction of translation of the transducer in a patient's body. Accordingly, each data point along horizontal axis of a longitudinal image 426 can have associated therewith a corresponding cross-sectional image 424. While FIG. 4 shows the axis representing transducer motion being the horizontal axis, it will be appreciated that such characteristics could alternatively describe a vertical axis, or any other orientation, and in some embodiments can generally be a longitudinal axis. In some embodiments, the longitudinal image 426 is essentially a side-view of a plurality of cross-sectional images stacked on one another and arranged according to their relative positions. In some embodiments, each of the cross-sectional images can include a small amount of longitudinal information, which can be used to fill in gaps between transducer positions from which image information was received.

The display 420 as shown in FIG. 4 can include image data 428. Image data 428 can include various pieces of information about the cross-sectional image 424, the longitudinal image 426, the patient being imaged, other system information, etc. In some examples, image data 428 can include the patient name, a patient ID number, the time and date, frame number, and/or image information acquisition parameters such as an imaging frequency. In various embodiments, image data 428 can be displayed collectively in a single location on the display 420, or can be displayed across various locations. In the example of FIG. 4, image data 428 is located in multiple locations. In some embodiments, the display 420 can include a real-time display while continually performing one or more imaging functions. The display 420 can include a user interface 430 to provide command and control functionality to the user.

In some embodiments, the display 420 shown in FIG. 4 is part of the intravascular processing engine. The display 420 can comprise a touch screen for user input and manipulation. In some embodiments, the user can perform various functions with regard to the generated display 420. In some examples, the user can manipulate the brightness and/or contrast of the display 420, save a screenshot to memory, initiate an imaging function such as a pullback operation, terminate an imaging function, and so on. In the case of a longitudinal image 426, in some embodiments, a user can select a point along the longitudinal axis in the longitudinal image 426 for which to display the associated cross-sectional image 424 of the corresponding transducer position.

Exemplary intravascular systems and methods including position sensors are described in U.S. patent application Ser. No. 14/143,801, filed Dec. 30, 2013, and entitled "Position sensing in intravascular imaging," which is assigned to assignee of the present application and is hereby incorporated by reference herein in its entirety.

Figure 5A:
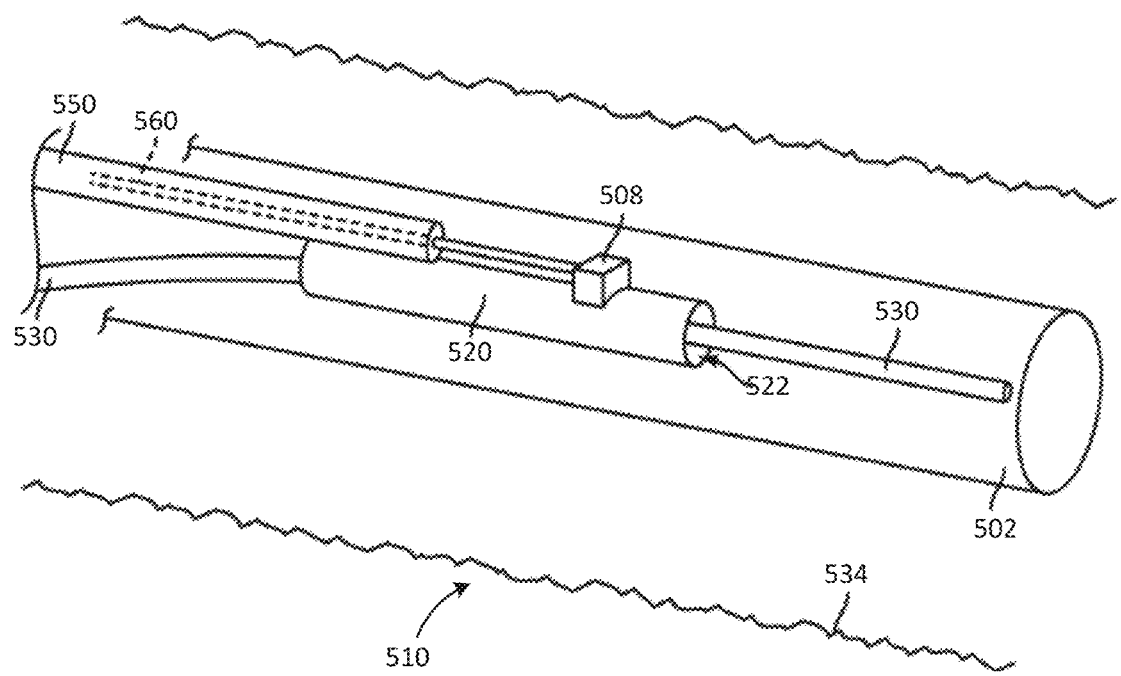
FIGS. 5A and 5B are perspective views of a sensor delivery device for measuring a physiological parameter in a patient.

Other exemplary systems such as 100 shown in FIG. 1 may include MPS systems. FIG. 5A is an exemplary MPS system including a sensor delivery device 510. The MPS system of FIG. 5A includes a distal sleeve 520 having a guidewire lumen 522 for slidably receiving a medical guidewire 530. A sensor 508 is coupled to the distal sleeve 520, sensor 508 being capable of sensing and/or measuring a physiological parameter of a patient and generating a signal representative of the physiological parameter. Thus, the distal sleeve 520, and hence, the sensor 508, may be positioned within a patient (e.g., within an anatomical structure of a patient, such as within a vein, artery, or other blood vessel, or across a heart valve, for example) by causing the distal sleeve 520 to slide over the medical guidewire 530 to the desired position.

The sensor delivery device 510 of FIG. 5A also includes a proximal portion 550, which is coupled to the distal sleeve 520. The proximal portion 550 includes a communication channel 560 for communicating the signal from the sensor 508 to a location outside of the patient (e.g., to processing engine 112 or display 114 of FIG. 1, or other computer, monitor, or another medical device). Communication channel 560 may comprise a fiber optic communication channel in certain preferred embodiments, such as where the sensor 508 is a fiber optic pressure sensor. Alternately, communication channel 560 may comprise an electrically conductive medium, such as one or more electrical conducting wires. Of course, many other forms of communication media may be suitable for transmitting the signal generated by sensor 508 to a location outside of the patient. In some embodiments of the invention, the communication channel 560 may comprise any of a variety of fluid and/or non-fluid communication media, such as a wireless communication link, or an infrared capability, or acoustic communications such as ultrasound, as possible examples.

During operation of the exemplary MPS system, the proximal portion 550 is also adapted to assist an operator (e.g., a physician or other medical staff) in positioning the distal sleeve 520 and the sensor 508 within an anatomical (e.g., vascular) structure of the patient. This is typically accomplished by an operator first inserting a "standard" medical guidewire 530 into a patient's vasculature and advancing it past an area of interest. The sensor delivery device 510 is then deployed by "threading" the distal sleeve 520 onto the guidewire 530 such that the lumen 522 slides over the guidewire 530, and advancing the distal sleeve 520 (and the associated sensor 508) by moving (e.g., pushing and/or pulling) the proximal portion 550 until sensor 508 is in the desired location.

The device 510 and the guidewire 530 are typically manipulated inside a guiding catheter 502, which has been placed in the anatomical (e.g., vascular) structure of interest. In certain preferred embodiments of the invention, the guidewire lumen 522 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.010, 0.014, 0.018, 0.021, 0.025, 0.028, 0.032, 0.035, and 0.038 inches. Thus, in certain preferred embodiments of the invention, the guidewire lumen 522 may be sized appropriately to slide over a particular standard size medical guidewire. A device according to preferred embodiments of the invention may therefore be made available in a range of sizes corresponding to standard medical guidewire sizes.

One potential advantage of a sensor delivery device 510 according to embodiments of the invention is that it allows a physician to use the guidewire of their choice. Sensor delivery device 510 can be sized to be used with any guidewire. The physician may, for example, choose a particular guidewire based on its unique flexing and torque characteristics for certain procedures. Delivery device 510 according to various embodiments of the invention provides the physician with the ability to use whichever guidewire is deemed best suited for the particular application.

Another potential advantage of the sensor delivery device 510 is that it does not require repositioning of the guidewire in order to make sensor readings. Once the guidewire has been positioned across a stenotic lesion, for example, the sensor delivery device 510 can be positioned (e.g., advanced and/or retracted) over the guidewire and the sensor 508 can therefore be advanced and retracted across lesions to make pressure readings, for example, without moving the guidewire. A physician may also save time by not having to reposition the guidewire across the lesion or lesions to make such measurements.

In the example shown in FIG. 5A, the device 510 is being deployed using guiding catheter 502, which has been placed within a vascular structure of interest (in this example, blood vessel 534, which can be, for example, a coronary artery of the patient). In certain embodiments of the invention, the size or "footprint" (e.g., the width and/or the cross-sectional area) of device 510 may allow it to fit within certain standard sized guiding catheters. For example, in certain diagnostic applications, it would be desirable to have device 510 deployed within a certain sized guiding catheter (e.g., smaller than about 5 or 5 French (FR)).

In certain embodiments of the invention, the distal sleeve 520 of the device may be substantially concentric with the guidewire 530. The coupling of the proximal portion 550 to the distal sleeve 520 allows the guidewire 530 to separate from the rest of device 510 (e.g., in what is sometimes referred to as a "monorail" catheter configuration); this would typically occur inside the guiding catheter 502. The guidewire 530 and device 510 would both exit the patient at the proximal end of the guiding catheter 502 as separate devices. Having the device 510 and guidewire 530 separate allows the physician to independently control device 510 and guidewire 530, as necessary. It may also allow a physician to use a shorter guidewire for catheter exchange. For example, a monorail-type configuration may allow for the use of a guidewire that is approximately 170 to 200 cm long, whereas an "over-the-wire" configuration might require the use of a much longer (e.g., up to 500 cm or more) guidewire. Having the device 510 and guidewire 530 separate (except at the distal sleeve 520) may also result in less friction (e.g., within the guiding catheter 502) than if the device 510 and guidewire 530 had to be moved together as a unit. In some embodiments, a hydrophilic coating may be applied to various portions of the device to further reduce the amount of friction encountered, for example, when advancing or retracting device 510.

One diagnostic application in which various embodiments of the invention may be well-suited is the measurement of Fractional Flow Reserve (FFR). As noted above, the FFR measurement quantifies the degree to which a stenotic lesion, for example, obstructs flow through a blood vessel. To calculate the FFR for a given stenosis, two blood pressure measurements are needed: one pressure reading is taken on the distal side of the stenosis (downstream side), the other pressure reading is taken on the proximal side of the stenosis (upstream side). The FFR is therefore a unitless ratio of the distal pressure to the proximal pressure. The pressure gradient across a stenotic lesion is an indicator of the severity of the stenosis. The more restrictive the stenosis is, the more the pressure drop, and the lower the FFR.

Figure 5B:
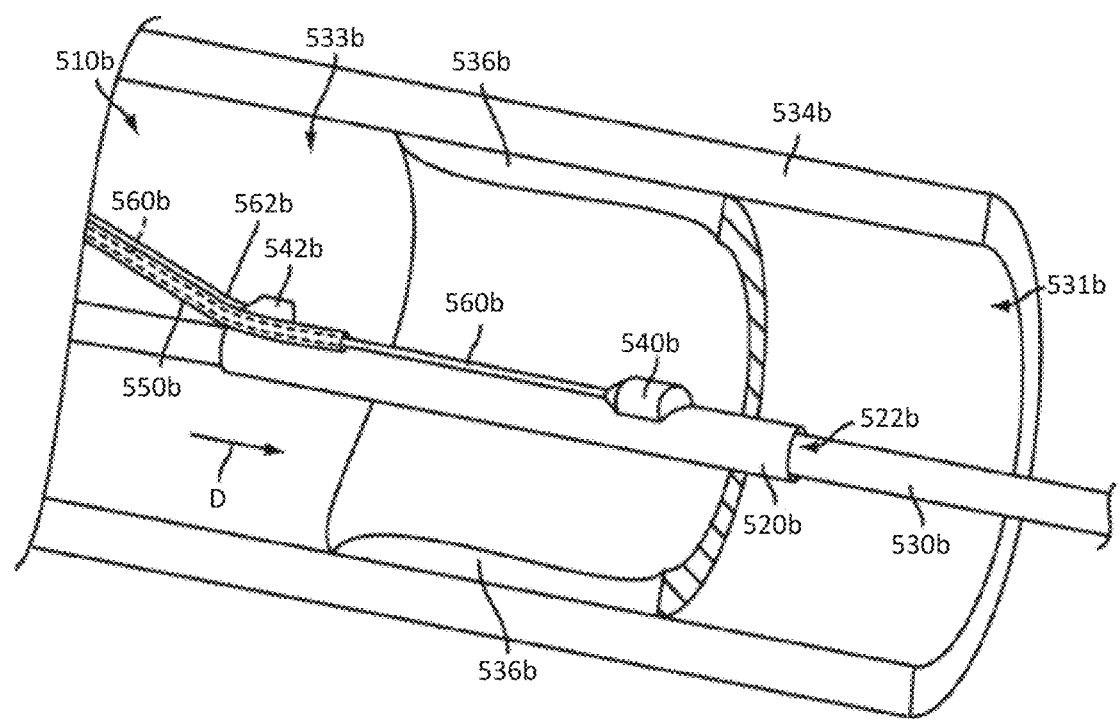

FIG. 5B is a perspective view of a sensor delivery device for measuring a physiological parameter in a patient according to an embodiment of the invention. The embodiment shown in FIG. 5B might, for example, be deployed to make an FFR measurement in a blood vessel of a patient. FIG. 5B shows a sensor delivery device 510$b$ being deployed in a blood vessel of a patient (e.g., coronary artery 534$b$) across a stenosis (e.g., stenotic lesion 536$b$). To make an FFR measurement, for example, first sensor 540$b$ may be positioned to measure distal (downstream) blood pressure, $P_d$, at a location 531$b$ downstream of a location of interest (e.g., stenotic lesion 536$b$). First sensor 540$b$ may then be positioned to measure proximal (upstream) blood pressure, $P_p$, at a location 533$b$ upstream of a location of interest (e.g., stenotic lesion 536$b$). FFR is simply calculated as the ratio of distal pressure to proximal pressure, or FFR=$(P_d/P_p)$. The use of the terms "downstream" and "upstream" are with respect to the normal direction of blood flow, "D," as shown in FIG. 5B.

In FIG. 5B, first sensor 540$b$ is coupled to distal sleeve 520$b$. In the embodiment shown in FIG. 5B, first sensor 540$b$ is coupled to an outer surface of distal sleeve 520$b$. The first sensor 540$b$ is adapted to measure a physiological parameter of a patient, such as a blood parameter (e.g., blood pressure, temperature, pH, blood oxygen saturation levels, etc.), and generate a signal representative of the physiological parameter. In certain preferred embodiments of the invention, the first sensor 540$b$ is a fiber optic pressure sensor adapted to measure blood pressure. An example of a fiber optic pressure sensor is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size) manufactured by Fiso Technologies, Inc. (Quebec, Canada). In certain alternate embodiments, first sensor 540b may be a piezo-resistive pressure sensor (e.g., a MEMS piezo-resistive pressure sensor), and in other embodiments, first sensor 540b may be a capacitive pressure sensor (e.g., a MEMS capacitive pressure sensor). A pressure sensing range from about −50 mm Hg to about +300 mm Hg (relative to atmospheric pressure) is desired for making most physiological measurements with sensor 540b, for example.

In embodiments of the invention using the Fabry-Perot fiber optic pressure sensor as the sensor 540b, such a sensor works by having a reflective diaphragm that varies a cavity length measurement according to the pressure against the diaphragm. Coherent light from a light source travels down the fiber and crosses a small cavity at the sensor end. The reflective diaphragm reflects a portion of the light signal back into the fiber. The reflected light travels back through the fiber to a detector at the light source end of the fiber. The two light waves, the source light and reflected light travel in opposite directions and interfere with each other. The amount of interference will vary depending on the cavity length. The cavity length will change as the diaphragm deflects under pressure. The amount of interference is registered by a fringe pattern detector.

FIG. 5B shows proximal portion 550b coupled to the distal sleeve 520b. The proximal portion 550b includes a communication channel 560b for communicating the physiological signal from the sensor 540b to a location outside of the patient (e.g., to a processor, display, computer, monitor, or to another medical device). The proximal portion 550b may preferably be formed of a material of sufficient stiffness in order to assist an operator (e.g., a physician or other medical staff) in positioning the distal sleeve 520b and the sensor 540b within an anatomical (e.g., vascular) structure of the patient.

One suitable material for the proximal portion 550b may be a stainless steel hypotube, for example. Depending on the application, the proximal portion 550b (sometimes also referred to as the "delivery tube") should typically be stiffer and more rigid than the distal sleeve 520b in order to provide a reasonable amount of control to push, pull and otherwise maneuver the device to a physiological location of interest within the patient. In interventional cardiology procedures, for example, at least a portion of the proximal portion 550b will be maneuvered within a guiding catheter positioned within the aortic artery. The proximal portion 550b in such an application should therefore be flexible enough to accommodate the arch of the aorta, while being rigid enough to push and pull the device. Accordingly, suitable materials for proximal portion 550b may also include (in addition to the aforementioned stainless steel hypotube) materials such as nitinol, nylon, and plastic, for example, or composites of multiple materials.

The communication channel 560b may be disposed along an outer surface of proximal portion 550b, or may be formed within the proximal portion 550b, as shown in FIG. 5B. For example, communication channel 560b may comprise a communication lumen that extends longitudinally through proximal portion 550b in some embodiments. Communication channel 560b may comprise a fiber optic communication channel in certain embodiments, such as where the sensor 540b is a fiber optic pressure sensor. Alternately, communication channel 560b may comprise an electrically conductive medium, such as electrical conducting wires, or other communication media suitable for transmitting the signal generated by sensor 540b. In preferred embodiments of the invention, the communication channel 560b comprises a non-fluid communication medium. In the embodiment shown in FIG. 5B, communication channel 560b (e.g., a fiber optic cable) extends distally beyond proximal portion 550b and is coupled to sensor 540b. The communication channel 560b in such an embodiment is at least partially housed within a communication lumen of the proximal portion 550b (e.g., a stainless steel hypotube).

FIG. 5B also shows an optional embodiment of the invention in which a second sensor 542b may be coupled to the device 510b. For example, a second sensor 542b may be coupled to proximal portion 550b such that the first and second sensor 540b, 542b are spaced apart sufficiently (e.g., a fixed distance apart) to span a stenotic lesion. This embodiment may offer the ability to measure FFR without having to reposition device 510b, since first sensor 540b can be placed distal of the stenotic lesion 536b to measure $P_d$, and second sensor 542b can be placed proximal of the stenotic lesion 536b to measure $P_p$. Second sensor 542b may have a communication channel 562b, which can be housed within proximal portion 550b, or can be disposed along an outside surface of proximal portion 550b, as shown in FIG. 5B, for example. Further, the ability to measure $P_d$ and $P_p$ substantially simultaneously may improve accuracy and/or reduce the effects of certain types of errors illustrated and described in U.S. Pat. No. 8,298,156, filed Sep. 11, 2009, and entitled "Physiological sensor delivery device and method," which is assigned to assignee of the present application and is hereby incorporated by reference herein in its entirety.

It should be noted that certain embodiments can have more than two sensors, and that the spacing between adjacent sensors in such embodiments may be varied to provide a variable spacing capability. In certain alternate embodiments of the invention, one or more sensors can be disposed on the proximal portion 550b with no sensors disposed on the distal sleeve 520b, for example. In some alternate embodiments, it may be desirable to have a plurality of sensors (two, or three, or four, or more sensors) spaced at known, fixed distances, disposed along the proximal portion 550b. This can, for example, provide the ability to measure $P_d$ and $P_p$ substantially simultaneously, regardless of lesion length, by selecting an appropriate pair of sensors (from among the plurality of sensors) placed across the lesion from which to obtain the $P_d$ and $P_p$ signals. Further, the sensors can have some form of radiopaque markings incorporated thereon (e.g., marker bands), which can provide a visual estimate of lesion size in conjunction with the measurement of physiological parameters (e.g., $P_d$ and $P_p$).

It should be realized that there are other applications in which physiological parameter measurements can be facilitated with the devices and/or methods described herein. Other possible embodiments and implementations of various exemplary MPS systems are described in U.S. Pat. No. 8,298,156 (referenced above).

Figure 6:
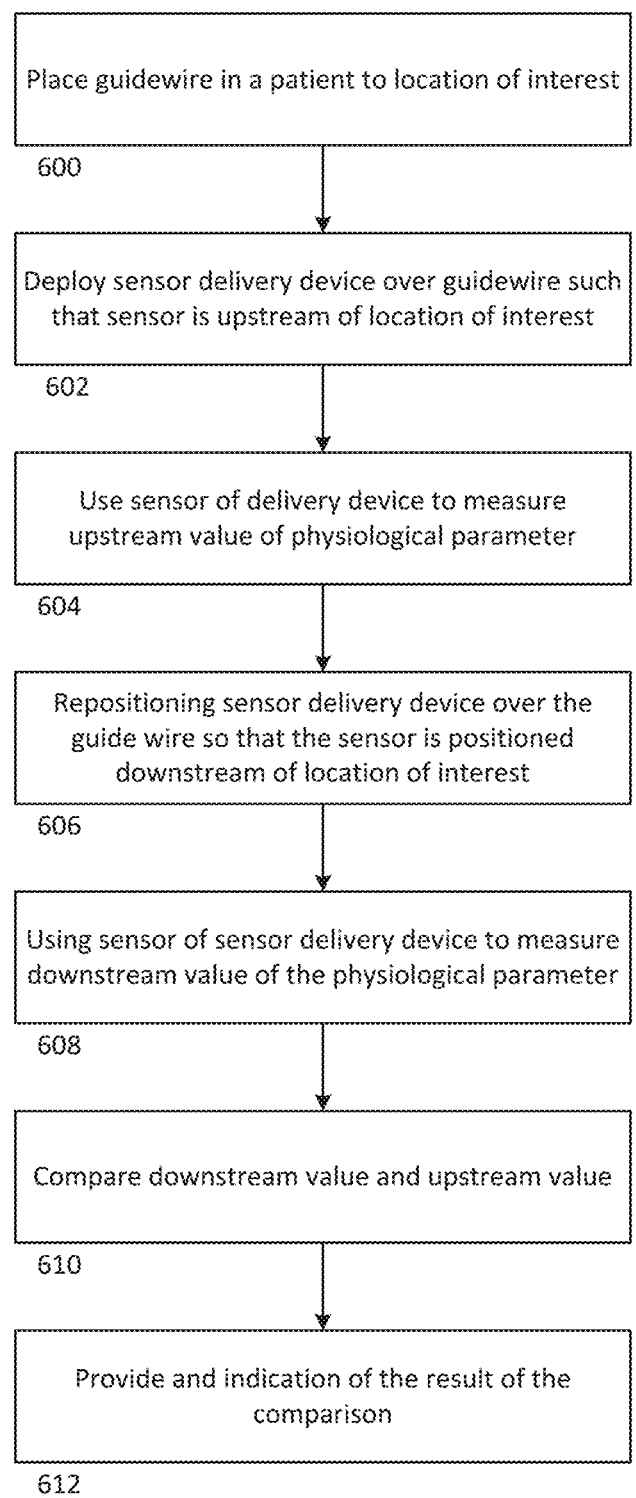
FIG. 6 is a process-flow diagram illustrating exemplary operation of an MPS system.

FIG. 6 is a process-flow diagram illustrating exemplary operation of an MPS system such as that shown in FIG. 5A or 5B. The ordering of the actions shown in FIG. 6 is for exemplary purposes only. In some embodiments, a system such as a powered injection system or a diagnostic monitoring system may be capable of performing some of the steps of the method shown in FIG. 6 automatically, or alternately, after the operator has requested that the method be commenced through manual activation on the control panel (or secondary panel, if available).

Step 600 in FIG. 6 comprises placing a guidewire in a patient to a location of interest, such as a stenotic lesion, or across a heart valve, for example. In some embodiments, this may be a diagnostic guidewire, and a guiding catheter may also be inserted into the patient in conjunction with the guidewire. Step 602 comprises deploying a sensor delivery device over the guidewire such that the sensor is positioned upstream of the location of interest (e.g., upstream of a stenotic lesion, or on the high pressure side of a valve). In some embodiments, the sensor delivery device will have a sensor mounted to a distal sleeve that slides over the guidewire, and a proximal portion that is used by an operator to advance the distal sleeve over the guidewire to the desired location without having to move the guidewire. Step 604 comprises using the sensor of the sensor delivery device to measure a value of the physiological parameter upstream of the location of interest. In some embodiments, the physiological parameter is blood pressure, and the pressure measured by the sensor upstream of a stenotic lesion is the proximal pressure, $P_p$.

In some examples, the $P_p$ measurement such as that made in step 604 may be normalized to a measurement obtained from an independent source. "Normalizing" the $P_p$ measurement refers to the fact that an independent source (e.g., a fluid sensor for monitoring patient blood pressure during a procedure) will be used to obtain the $P_p$ value that will be used for later comparisons or calculations with the $P_d$ value (e.g., the downstream pressure) measured with the sensor of the sensor delivery device. The normalizing step basically ensures that the $P_p$ value measured with the sensor equals the $P_p$ value measured using the independent source so that no error is introduced (or that any error is minimized) when a subsequent downstream pressure measurement (e.g., $P_d$) is made. An adjustment, if needed, can be made to either $P_p$ value, although it may often be simpler to adjust the sensor-based $P_p$ value to match the independent source's $P_p$ value.

Step 606 comprises repositioning the sensor delivery device over the guidewire such that the sensor is downstream of the location of interest (e.g., downstream of the stenotic lesion). Step 608 comprises using the sensor of the sensor delivery device to measure a downstream value of the physiological parameter. In some embodiments, this step comprises measuring blood pressure downstream of the stenotic lesion, $P_d$. Step 610 comprises comparing the measured value downstream of the location of interest (e.g., $P_d$, downstream blood pressure) to a value measured upstream of the location of interest using the independent source (e.g., $P_p$). In some embodiments, the comparison made in step 610 may comprise calculating a ratio of the two measured values. In some embodiments of the invention, step 610 comprises calculating FFR as the ratio of downstream to upstream blood pressures, $P_d/P_p$. Step 612, which may be an optional step, comprises providing an indication of the result of the comparison made in step 610. For example, step 612 may comprise providing an indication of the calculated FFR value (e.g., numerical or graphical display or plot), and/or other cues may be provided to an operator. A color-coded indication of the severity of a stenotic lesion may be provided, for example, a RED indicator for FFR values less than 0.75, and/or a GREEN indicator for FFR values equal to or greater than 0.75. Other examples of indicators are possible, including non-visual indicators—an audible indication, an alarm sound for example, can alert an operator of an FFR value that is less than 0.75, which may prompt the operator to make a therapy decision.

As with the exemplary IVUS systems and methods described above, an MPS procedure may include acquiring position information associated with a position of the sensor within the patient. For example, position information may be indicative of the position of the sensor relative to the patient or the lesion within the patient, or may include relative position information indicative of the relative difference in position between the upstream and downstream measurements. In various examples, position sensors such as those described above with respect to IVUS systems may be used, for instance, including a movable element and a reference element. The movable element may be configured to move relative to the reference element as the sensor moves within the patient.

In some examples, quantifying lesion severity in a diffusely affected coronary vessel may require a pressure pull-back curve indicating the pressure gradients within the vessel. This can be done by taking simultaneous pressure readings while withdrawing the pressure sensor (e.g., MPS) from a distal to a proximal position, for instance, during a steady-state maximum adenosine hyperemia. The resulting pressure data can be used to generate a corresponding pressure curve that represents the pressure gradient over the entire length of the vessel. Such pressure curves may demonstrate the exact location and severity of the lesion. In some instances, this pull-back curve can be extremely useful in guiding spot-stenting in a vessel with long and diffuse lesions.

Figure 7:
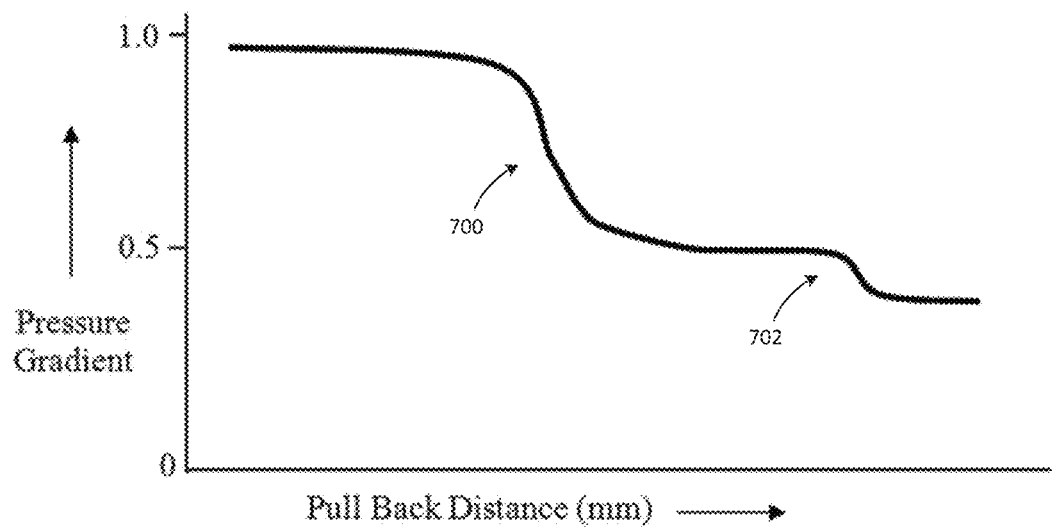
FIG. 7 is an exemplary plot showing a variety of pressure measurements associated with a variety of corresponding positions within a blood vessel of a patient.

Accordingly, in some examples, a plurality of measurements (e.g., pressure measurements, pressure gradients, etc.) may be acquired at a plurality of locations within the patient's vasculature. Such the relative positions at which such measurements are acquired may be determined, for example, using position information from the position sensor. The processing engine 112 may act to effectively combine measurement information and associated position information. The plurality of measurements may be displayed together with reference to the relative position at which each measurement was taken, such as on display 114. FIG. 7 is an exemplary plot showing a variety of pressure measurements associated with a variety of corresponding positions within a blood vessel of a patient.

Such data may be useful in identifying the positions of lesions or other pressure-affecting features within a blood vessel. For example, in some instances, severe gradients in pressure vs. position may be indicative of severe lesions within the vessel. In the illustrated example of FIG. 7, a first pressure gradient 700 may be indicative of a severe lesion in the vessel. A second, less severe gradient 702, may be indicative of a more minor lesion within the vessel. Accordingly, data such as that shown in FIG. 7 may be used to locate lesions within the patient's blood vessel. In some such embodiments, position information associated with the pressure data may be used to locate the location of the lesion in order to provide effective therapy at the lesion location. In some examples, the acquisition of pressure data over a distance such as shown in FIG. 7 may be useful for decision-making with regard to diagnosis and treatment of patients, such as those with complex coronary disease. The data may be particularly useful for determining which lesions within the patient should be treated and which need not be.

In some instances, pullback of the pressure sensor is done very slowly to capture pressure readings over the course of one or more heartbeats at each location. In some embodiments, to speed up the pullback, short interval instantaneous pressure measurements from multiple sensors can be recorded, such as sensors 540*b* and 542*b* of FIG. 5B. The multiple pressure recordings can be normalized to one of the readings to get a relative pressure gradient using a much shorter time interval at each measurement location.

Figure 8:
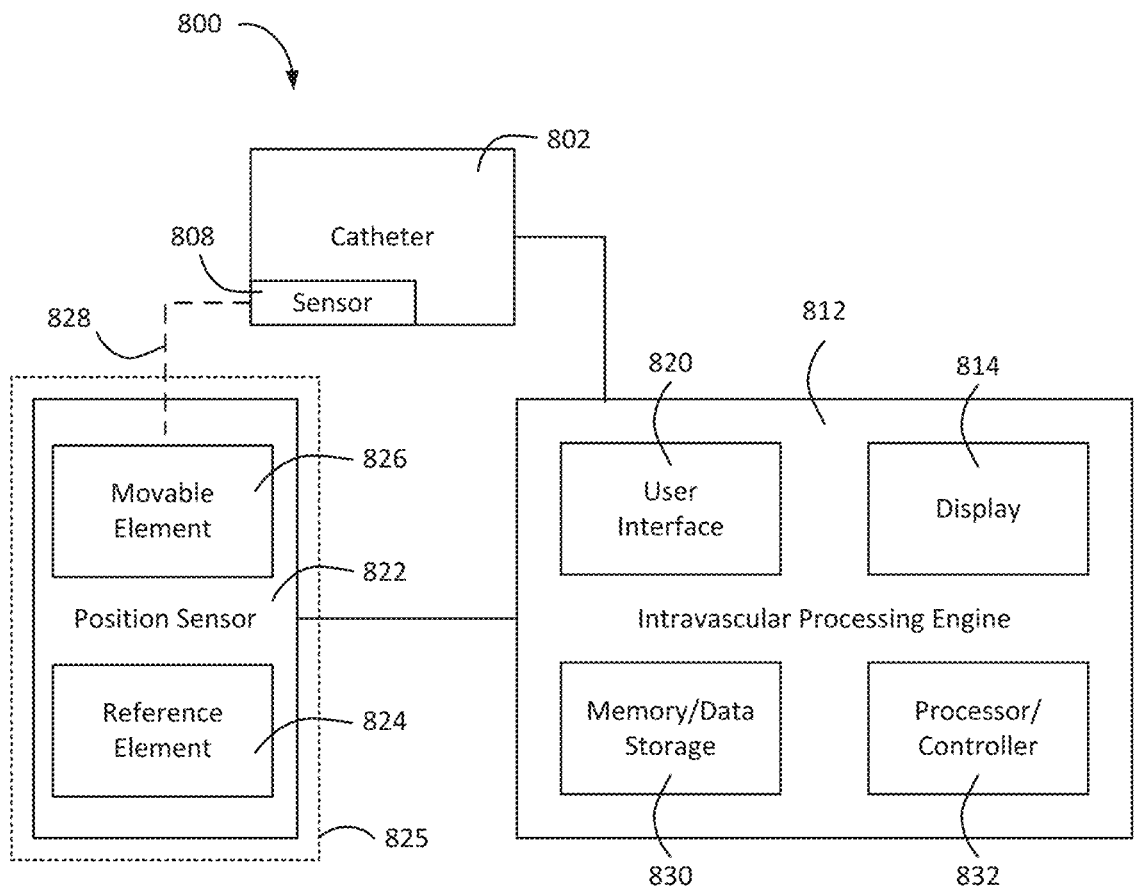
FIG. 8 is a system-level block diagram of an embodiment of an intravascular system that includes a position sensor.

As previously discussed, in many intravascular procedures, it can be advantageous to know at least relative position information regarding the location of various aspects of the system. FIG. 8 is a system-level block diagram of an embodiment of an intravascular system that includes a position sensor. In particular, the illustrative system 800 of FIG. 8 comprises a catheter 802, a position sensor 822 and an intravascular processing engine 812. The catheter 802 can include a sensor 808 and can be in communication with the processing engine 812. In some embodiments, the processing engine 812 is in direct communication with the sensor 808. In the embodiment of FIG. 8, the processing engine 812 comprises a display 814, a user interface 820, memory/data storage 830 and a processor/controller 832. These components may be integrated into, for example, a touch screen display and/or a computer.

In some embodiments, the catheter 802 or the sensor 808 within the catheter 802 can be translated within a patient's vasculature while performing a diagnostic or therapeutic function. In such cases, the processing engine 812 can receive information from the sensor 808 at a plurality of positions. In some embodiments, processing engine 812 can receive the information from a plurality of sensor positions and construct an aggregate data set. For example, in the case of an IVUS system, image data associated with a plurality of locations may be aggregated to construct a figure such as in FIG. 4. In the case of an MPS system, pressure or other data may be aggregated to generate a plot such as is shown in FIG. 7. Such aggregate data sets may be processed for presentation on a display 814 that comprises information from at least a subset of the plurality of sensor 808 positions. To construct such an aggregate set of information, it can be useful for the processing engine 812 to detect at least a relative relationship between the positions from which the information was received. Accordingly, some embodiments of the intravascular system 800 include a position sensor 822.

The position sensor 822 shown in FIG. 8 may include a movable element 826 and a reference element 824. The position sensor 822 can comprise, for example, a potentiometer, an encoder, a linear variable differential transformer, or other suitable position sensor. Such a position sensor 822 can be integrated into the intravascular system 800 and placed in communication with the processing engine 812. The movable element 826 of the position sensor 822 can have a movable element position that is correlated to the position of the sensor 808. The correlation between the sensor position and the position of the movable element 826 is represented by broken line 828 in FIG. 8. The reference element 824 of the position sensor 822 can be substantially fixed relative to motion of sensor 808 during a variety of intravascular processes (e.g., ultrasonic imaging, pressure sensing, etc.). In such embodiments, because of the correlation between the sensor position and the movable element position, the position sensor 822 can be configured to determine the relative motion of the sensor 808 with respect to the reference element 824 of the position sensor 822. In some embodiments, the position sensor 822 can determine the relative motion of the sensor 808 with respect to the reference element 824, which the position sensor 822 can communicate to other components of the processing engine 812.

As shown in FIG. 8, the position sensor 822 can be in communication with the processing engine 812. In some embodiments, the processing engine 812 can be configured to receive position information from the position sensor 822. Position information can comprise information regarding the position of the movable element 826 of the position sensor 822 relative to the reference element 824. The position information can include information received from an encoder, resistance information or other electrical data from a potentiometer, or any other signals or information from various kinds of position sensors. In embodiments in which the position sensor 822 determines the relative motion of the sensor 808 with respect to the reference element 824, the position sensor 822 can provide that position information to the processing engine 812. In some embodiments, the position sensor 822 can provide information regarding the movable element 826 and the reference element 824 to the processing engine 812, and the processing engine 812 can determine the relative motion of the sensor 808 with respect to the reference element 824. As discussed, the position of the movable element 826 can be correlated to the position of the sensor 808 of the catheter 802. In some embodiments, the position sensor 822 can compare the location of the movable element 826 with that of the reference element 824, account for how the location of the movable element 826 correlates to that of the sensor 808, and determine the location of the sensor 808 relative to that of the reference element 824. In such embodiments, the position sensor 822 can provide the location of the sensor 808 to the processing engine 812. In some embodiments, the position sensor 822 can simply send information concerning the location of the movable element 826 relative to that of the reference element 824 to the processing engine 812. In some such embodiments, the processing engine 812 can compare the location of the movable element 826 with that of the reference element 824, account for how the location of the movable element 826 correlates to that of the sensor 808, and determine the location of the sensor 808 relative to that of the reference element 824. In other embodiments, the processing engine 812 may measure the motion of the movable element 826 relative to the reference element 824 and determine the motion of the sensor therefrom.

In some embodiments, the processing engine 812 can be configured to receive both sensor information (e.g., image information from IVUS transducer, pressure information from a pressure sensor such as an MPS, etc.) from the intravascular catheter 802 and position information from the position sensor 822. The processing engine 812 can associate particular image information with a relative position of the sensor 808. The processing engine 812 can be configured to generate a display based on the sensor information and the position information.

The processing engine 812 can receive and process sensor information and position information corresponding to multiple longitudinal positions within the blood vessel being analyzed. In some configurations, the processing engine 812 can receive a first set of sensor information and a first set of position information, each corresponding to a first movable element position. The processing engine can additionally receive a second set of sensor information and a second set of position information, each corresponding to a second movable element position. In general, the sensor information and position information can comprise information corresponding to any number of movable element positions. In some preferred embodiments, the processing engine 812 can process sensor information and position information in real time for several locations during translation of the sensor to display real-time data regarding the blood vessel being analyzed.

As discussed elsewhere herein, in some embodiments the movable element position is correlated to the position of the sensor 808. Thus, first and second sets of sensor and position information corresponding to first and second movable element positions can also correspond to first and second sensor 808 positions. The sensor 808 can be translated within the patient's vasculature to various positions, while the movable element 826 can move relative to the reference element 824 correspondingly. The sensor 808 can be translated through the patient's vasculature in a number of ways. In some embodiments, the catheter 802 translates through the patient's vasculature. The sensor 808 can translate within the catheter 802, within a sheath, for example. In some embodiments, the intravascular imaging system can include a translation mechanism configured to translate the catheter 802 and/or the sensor 808 within the catheter 802.

In various embodiments, elements of the position sensor 822 may be positioned in various portions of a system. For instance, in some examples, one or both of the movable element 826 and the reference element 824 may be included on a translation mechanism. Additionally or alternatively, one or both of such elements may be disposed on or otherwise integrated into catheter 802. In some examples, the system 800 may include a dedicated position sensor assembly 825 for housing or otherwise supporting at least a portion of the position sensor 822.

Figure 9:
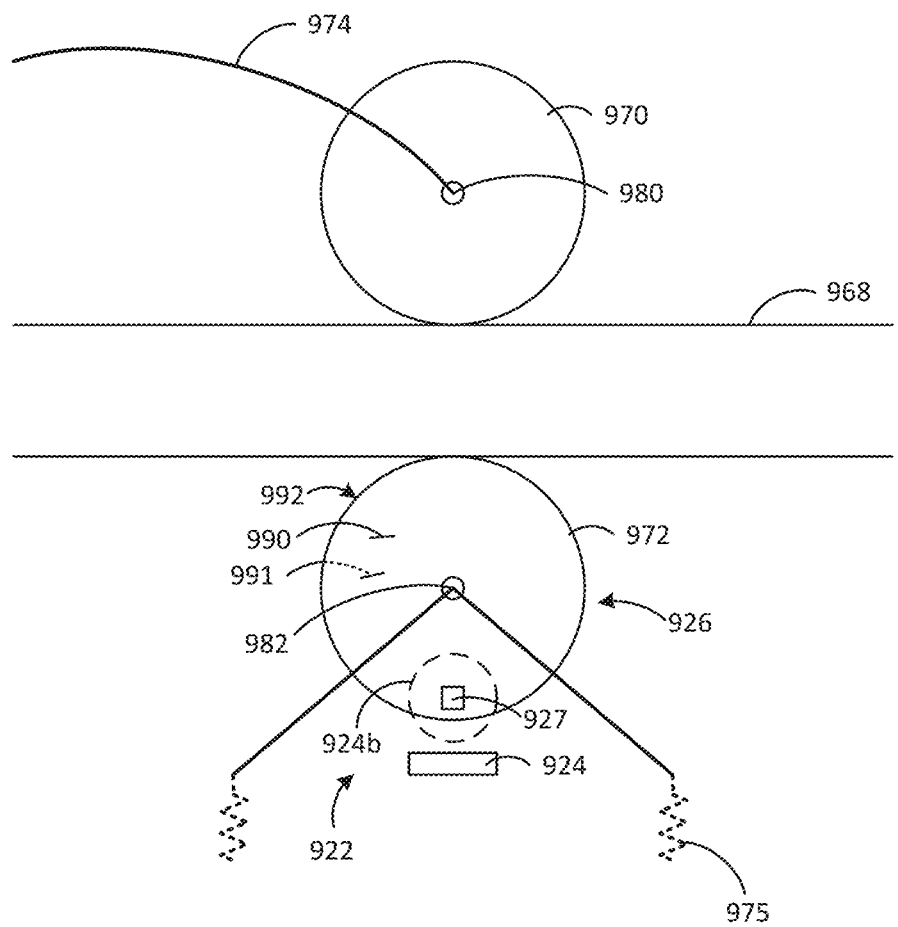
FIG. 9 is a diagram of an exemplary position sensor configuration including multiple friction wheels.

FIG. 9 is a diagram of an exemplary position sensor configuration. As shown in the illustrated embodiment, friction wheels 970, 972 engage cable 968 of a catheter. The cable 968 may include any element of the system that moves relative to a sensor (e.g., 108 in FIG. 1) of the catheter. In some examples, the sensor may include an IVUS transducer or a pressure sensor (e.g., MPS). In some such systems, cable 968 may include the drive cable (e.g., 268 of FIG. 2) of an IVUS system catheter or a proximal portion (e.g., 550) of a sensor delivery device (e.g., 510 of FIG. 5A) in an MPS system. Other movable portions of the catheter or system may be used as cable 968.

In various embodiments, friction wheels 970, 972 may be secured to a portion of the system that is fixed relative to the patient during operation. For example, friction wheels 970, 972 may be secured to the base 949 of translation element 942. In some examples, the system can include a position sensing assembly configured to support various system components, such as one or more aspects of position sensor 922.

In some examples, friction wheels 970, 972 include opposing flat edges 990, 991 and a circumferential edge 992 extending therebetween. In some such embodiments, the perimeter of friction wheels 970, 972 is substantially circular and the circumferential edge 992 is a single continuous edge. In some embodiments, friction wheels 970, 972 include a material having a high coefficient of friction relative to cable 968. In various embodiments, the entire friction wheel may be made of the high-friction material. In other embodiments, the circumferential edge 992 may include the high-friction material while the remaining surfaces e.g., 990, 991) of the friction wheels 970, 972 do not.

During operation, as the sensor (e.g. 108) moves within the patient, cable 968 similarly moves proximally or distally. In some examples, because of the engagement between the high-friction material on the circumferential edge 992 of friction wheels 970 and 972 and the cable 968, proximal or distal movement of the cable 968 causes friction wheels 970 and 972 to rotate about axes 980 and 982, respectively. In some embodiments, friction wheel 970 may be attached to a bias spring 974 configured to press friction wheel 970 against cable 968. The increased force between the friction wheel 970 and the cable 968 caused by spring 974 may prevent the cable 968 from slipping relative to the friction wheels 970, 972 when moving proximally or distally.

In some embodiments, one more friction wheels may include at least a part of the position sensor 922. In the illustrated embodiment, friction wheel 972 includes a movable element 926 of position sensor 922. Movable element 926 may include one or more detectable elements 927 such as optically or magnetically detectable elements. In some such embodiments, the reference element 924/924b of the position sensor 922 may be positioned proximate the friction wheel 972. The illustrated example of FIG. 9 shows reference element 924 positioned proximate the friction wheel 972. Reference element 924 may include a magnetic or optical detector (e.g., encoder) capable of detecting motion of the movable element 926, for example, when the detectable element 927 moves past the reference element 924. Additionally or alternatively, reference element 924b may be positioned above friction wheel 972 for detecting the movable element 926. The position of the reference element (e.g., at 924 or 924b) may be chosen for best detecting the type of detectable element 927 on the movable element 926 (e.g., optical, magnetic, etc.). For example, in some configurations, reference element 924b, positioned above friction wheel 972, may be best suited for detecting an optically detectable movable element 926.

In such a configuration, as the cable 968 (and sensor, e.g., 108, attached thereto) moves proximally or distally, movement between the movable element 926 and reference element 924 can be monitored as the friction wheel(s) rotate. Detected motion between movable element 926 and reference element 924 can be used to determine the amount of rotation of the friction wheel(s). Since the cable 968 rotates the friction wheel(s) without slipping, the amount of rotation of the friction wheel(s) is directly correlated to linear distance moved proximally or distally by the cable 968, and similarly, the sensor. Thus, as described previously, motion between the movable element 926 and the reference element 924 can be detected and used to determine the relative position and motion of the sensor within the patient.

In some examples, movable element 926 comprises a plurality of detectable elements (e.g., 927). In some embodiments, at least two of the plurality of detectable elements are distinguishable from one another by an output of the reference element 924. For example, a plurality of magnetically detectable elements may have different magnetic properties, such as magnetization strength or direction. Such differences may be detectable via an encoder sensing the magnetic field output from the detectable elements. By spacing these detectable elements apart in certain ways and/or arranging them in certain orders, an output signal from the reference element 924 may indicate the direction of rotation of the friction wheel(s), and thus the direction of motion of the sensor. In some examples, each of a pair of friction wheels (e.g., 970, 972) may include detectable elements detectable by at least one detector. The detectable elements on the separate friction wheels may be positioned in order to enable the determination of the direction of motion of the sensor within the patient. Additionally or alternatively, position sensor 922 may include other ways to determine the direction of rotation of friction wheel(s).

In some examples, position sensor may include a single friction wheel, such as 972. In some such examples, the single friction wheel (e.g., 972) may be biased by one or more springs (e.g., 975) against the cable 968. The force of the spring(s) 975 pressing the wheel 972 against the cable may cause the single friction wheel 972 to rotate in response to proximal or distal motion of the cable 968. Alternatively to spring 975, a spring biasing arm such as 974 may be used to provide added force between a friction wheel 972 and the cable 968.

It will be appreciated that detectable element 927 need not be disposed directly on friction wheel 972 as shown. Rather, in some embodiments, one or more friction wheels such as 970, 972 may include additional components and cause such additional components to rotate. In some such examples, detectable element 927 may include or be included on one or more such additional components. In general, the network of one or more friction wheels, as well as any additional components associated therewith that cause the detectable element 927 to move relative to the reference element 924 may be considered to be a part of movable element 926.

Figure 10:
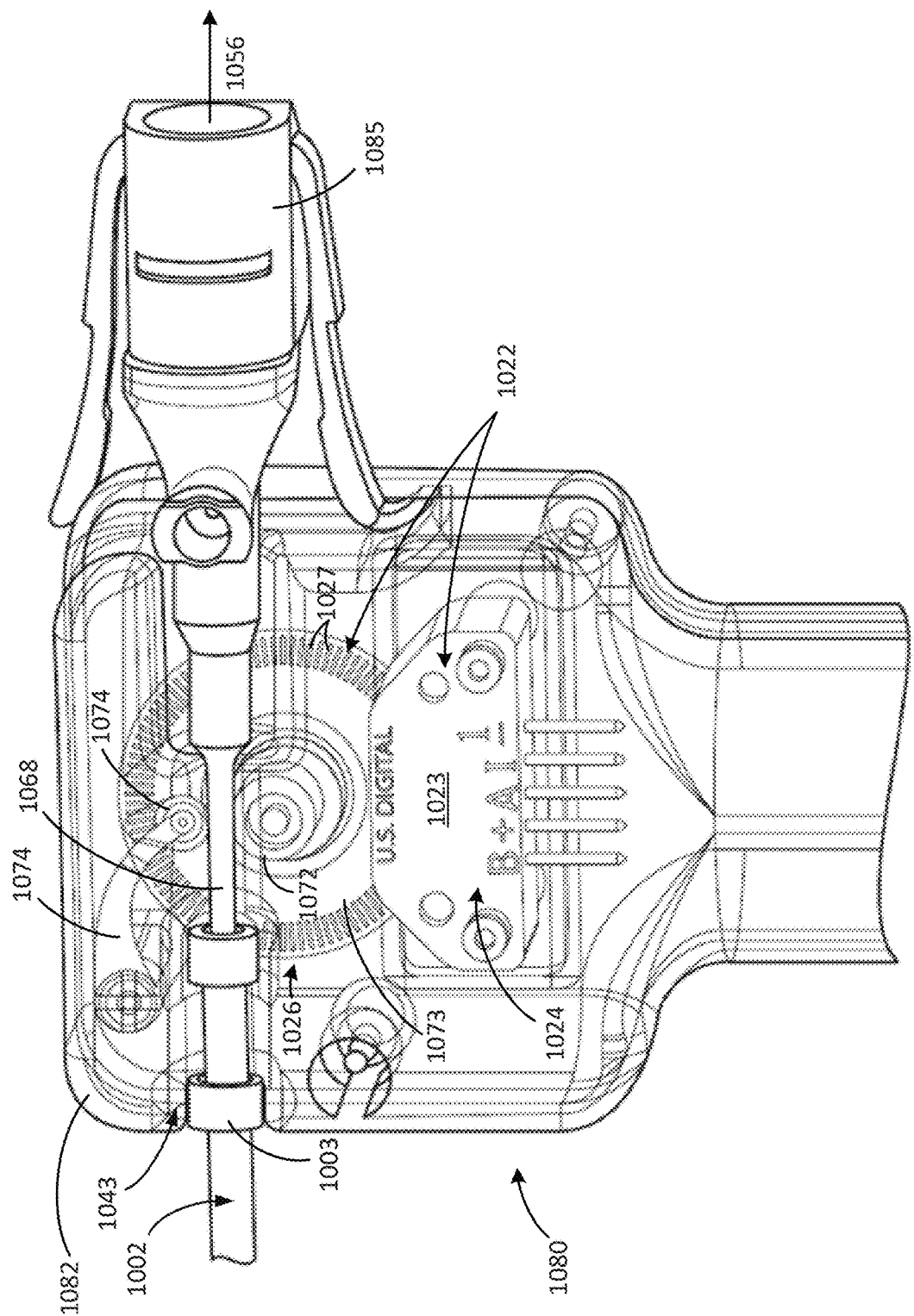
FIG. 10 is a cross-sectional view of an exemplary intravascular catheter system including multiple friction wheels.

FIG. 10 is a cross-sectional view of an exemplary intravascular catheter system including friction wheels such as illustrated in FIG. 9. As described above, in some examples, the system can include a dedicated position sensing assembly 1080 configured to house position sensor 1022. In some such examples, the position sensing assembly 1080 may include a housing 1082 with a groove 1043 for receiving an anchor 1003 of the catheter 1002. In the illustrated embodiment, the catheter 1002 further includes a cable 1068 extending proximally through the position sensing assembly 1080 to a connector 1085 for interfacing with an attachment point 1056, for example, of an intravascular processing engine.

In the illustrated embodiment, cable 1068 engages with friction wheels 1070, 1072 within the housing 1082 of the position sensing assembly 1080. Friction wheel 1070 is attached to bias spring 1074 which presses the drive cable between friction wheels 1070, 1072. As described previously with regard to FIG. 9, proximal or distal motion of the cable 1068 causes the friction wheels to rotate. In the illustrated embodiment, friction wheel 1072 includes disc 1073. Disc 1073 includes a plurality of detectable elements 1027 disposed about the circumference of the disc and which can be detected by encoder 1023. In some examples, detectable elements 1027 may include magnetically or optically detectable elements, while encoder 1023 may include the ability to detect one or both of magnetically and optically detectable elements. In some embodiments, system may include a light source (not shown) configured to emit light toward disc 1073 opposite a detection element of the encoder 1023. In some such examples, the detectable elements 1027 on disc 1073 includes apertures extending through disc 1073 so as to allow light to pass therethrough. Thus, the encoder 1023 may be configured to detect light that is transmitted through apertures in the disc 1073.

Thus, in the illustrated embodiment, as the cable 1068 moves proximally or distally (similarly moving the sensor), friction wheels 1070, 1072 rotate. Rotation of friction wheel 1072 causes rotation of disc 1073, while encoder 1023 detects the rotation of the disc 1073 by detecting the detectable elements 1027. In such an embodiment, friction wheel 1072, including disc 1073 and detectable elements 1027, may together make up the moveable element 1026 of a position sensor capable of detecting relative position and motion of the sensor of catheter 1002. The reference element 1024 of the position sensor may comprise encoder 1023 configured to detect the rotation of disc 1073 by detecting detectable elements 1027.

In an exemplary embodiment, encoder 1023 is configured to detect detectable elements 1027 as the friction wheel 1072 rotates. In some embodiments, the encoder 1023 outputs a signal (e.g., a high signal or a low signal) upon detecting one of detectable elements 1027 and outputs a different signal (e.g., a low signal or a high signal) when a detectable element 1027 is not detected. The processing engine may receive the signals from the encoder 1023 and use the series of signals to determine the rotation of the friction wheel 1072. For example, the processing engine may be programmed with information associating the amount of rotation of friction wheel 1072 and a number of detected detectable elements 1027. For example, detectable elements 1027 may be disposed periodically about a portion of the friction wheel 1072 (e.g., disc 1073 or the wheel 1072 itself). Thus, each detected area corresponds to a certain fraction of rotation of the friction wheel 1072. The amount of rotation of the friction wheel 1072 may be used to determine the linear distance moved at a certain radius of the friction wheel 1072, such as at an edge that engages the cable 1068. Thus, assuming no slipping between the cable 1068 and friction wheel 1072, the linear distance moved by the cable 1068 may be determined.

Accordingly, in such embodiments, the number of detectable elements 1027 detected by the encoder 1023 corresponds to the linear movement of the cable 1068, which corresponds to the motion of the sensor within the patient. In various embodiments, the processing engine may be programmed with any variety of calibrated relationships. For example, the processing engine may be programmed with information associating a number of detected detectable elements 1027 with an amount of rotation of the friction wheel 1072 or an amount of linear motion of the cable 1068 and/or the sensor associated therewith. Thus, the number of detectable elements 1027 detected by the encoder may be used to determine the amount of motion of the sensor through a patient's blood vessel.

In some examples, position sensor 1022 produces a signal indicative of the direction of rotation of the friction wheel 1072, which may correspond to the direction of motion of the sensor within the patient. For instance, in some embodiments, some different detectable elements 1027 may be distinguishable from one another, such as by the output produced to the processing engine. In some such embodiments, the intravascular processing engine may be programmed with instructions to determine the direction of rotation of the friction wheel 1072 based on the order of distinguishable detectable elements 1027 detected by encoder 1023. In some embodiments, friction wheel 1070 may include one or more detectable elements that may assist in determining the direction of rotation of the friction wheels 1070, 1072. For example, detectable elements (not shown) on friction wheel 1070 may be positioned so that they are detected at different times relative to the detection of detectable elements 1027 on friction wheel 1072 depending on the direction of rotation. Thus, the timing of detected detectable elements from different friction wheels may be used to determine the direction of rotation of the friction wheels, and thus the direction of motion of the sensor within the patient's blood vessel. Additionally or alternatively, position sensor 1022 may include an additional sensing element (not shown) configured to determine the direction of rotation of one or both of friction wheels 1070, 1072 and/or the direction of motion of the cable 1068.

While shown as being included in a standalone position sensing assembly 1080, it will be appreciated that the friction wheels (e.g., 1070, 1072) and associated components (e.g., encoder 1023) may be integrated into a variety of locations in an intravascular system. For instance, such components may be integrated into a translation element or other catheter interface element (e.g., 110 of FIG. 1) or into a valve facilitating the insertion of the catheter into the patient (e.g., a hemo stasis valve).

Various friction wheel configurations have been described. Position information acquired from a position sensor associated with the friction wheels may be acquired by the processing engine for associating with corresponding intravascular data. In various embodiments, such position data may be associated with image data acquired from an IVUS transducer or pressure data acquired from a pressure sensor (e.g., an MPS). Resulting sets of associated data (e.g., position and image data, position and pressure data, etc.) may be used to generate sets of data such as an IVUS longitudinal image (e.g., 426 in FIG. 4) or a pressure-position plot (e.g., plot of FIG. 7). Such information may be used by the system operator to more precisely analyze the status of a patient. This may allow for a more detailed diagnosis and a more precisely defined treatment plan. In some cases, the data may be used to determine a most effective treatment location within the patient, and in some further examples, to execute a treatment at the determined location.

Various aspects of the invention can be embodied in a non-transitory computer-readable medium. A non-transitory computer-readable medium can comprise executable instructions for causing a processor to receive sensor information from a sensor (e.g., 108) located near the distal end (e.g., 106) of an intravascular catheter (e.g., 102), and position information from a position sensor (e.g., including one or more friction wheels). The position sensor can comprise a movable element and a reference element and the position information can comprise a movable element position, representing the position of the movable element relative to the reference element and correlated to the sensor position. The non-transitory computer-readable medium can further contain executable instructions to cause the processor to associate sensor information with position information corresponding to the location at which the sensor information was acquired. In some embodiments, the non-transitory computer-readable medium may generate a display based on the received sensor information and position information. For example, a longitudinal image comprising position information and corresponding image information from an IVUS catheter may be generated. In other examples, a pressure vs. distance curve comprising position information and corresponding pressure information from a pressure sensor (e.g., MPS) may be generated. In some embodiments, the non-transitory computer-readable medium can be embodied in the processing engine 112. In some embodiments, a non-transitory computer-readable medium can comprise executable instructions for causing a processor to perform any method discussed herein.

It should be appreciated that components described with regard to particular embodiments of the invention may be combined to form additional embodiments. Instructions embedded or encoded in a computer-readable storage medium may cause a programmable processor, or other processor, to follow the instructions prescribed. Computer readable storage media may include random access memory (RAM), read only memory (ROM), a hard disk, optical media, or other computer readable media.

Various embodiments have been described. Such embodiments are exemplary and do not limit the scope of the invention in any way. Rather, these and others are within the scope of the following claims.

The invention claimed is:

1. An intravascular system comprising:
   a catheter including a proximal end, a distal end, a sensor located at the distal end, and a cable extending from the proximal end of the catheter to the distal end of the catheter and operatively connected to the sensor at the distal end, the sensor configured to provide an intravascular signal representative of one or more intravascular properties of a patient;
   a first friction wheel and a second friction wheel positioned generally opposite one another such that the cable of the catheter extends between the first friction wheel and the second friction wheel, wherein distal and proximal motion of the cable causes rotation of the first friction wheel and the second friction wheel;
   a disc coaxially aligned with the first friction wheel, the disc configured to rotate with the first friction wheel and in a same direction as the first friction wheel, the disc having a radius larger than a radius of the first friction wheel;
   a first position sensor including a first reference element and a first plurality of detectable elements, the first plurality of detectable elements being disposed about a circumference of the disc, wherein each of the first plurality of detectable elements have a distinguishable magnetic strength or magnetic direction from every other detectable element of the first plurality of detectable elements, the first position sensor configured to generate a first position signal based on the first reference element directly detecting the distinguishable magnetic strength or magnetic direction of a first detectable element of the first plurality of detectable elements moving relative to the first reference element and based on previously directly detecting the distinguishable magnetic strength or magnetic direction of a second detectable element of the first plurality of detectable elements, the first plurality of detectable elements configured to move relative to the first reference element in response to rotation of the disc and the first friction wheel;
   a second position sensor including a second plurality of detectable elements and being configured to generate a second position signal, the second friction wheel including the second plurality of detectable elements; and
   an intravascular processing engine in communication with the sensor of the catheter and the first position sensor and configured to receive the intravascular signal from the sensor of the catheter, the first position signal from the first position sensor, and the second position signal from the second position sensor, and
   wherein a direction of motion of the cable of the intravascular catheter is determined based on the first position signal and the second position signal that correspond to the detectable elements of the first plurality of detectable elements being detected at different times relative to detection of the second plurality of detectable elements.

2. The system of claim 1, wherein the second friction wheel is spring-biased against the catheter cable.

3. The system of claim 1, wherein the catheter comprises an intravascular ultrasound (IVUS) catheter, the sensor of the catheter comprises an IVUS transducer, and the cable comprises a drive cable.

4. The system of claim 3, wherein the processing engine is configured to receive image information from the IVUS transducer and position information from the first position sensor and the second position sensor to generate a longitudinal IVUS image.

5. The system of claim 1, wherein the catheter comprises a monorail pressure sensor (MPS) catheter having a proximal portion, the sensor comprises a pressure sensor, and the cable comprises the proximal portion of a sensor delivery device.

6. The system of claim 5, wherein the processing engine is configured to receive pressure information from the pressure sensor at a plurality of locations within the patient and position information from the first position sensor and the second position sensor associated with the pressure information at each of the locations.

7. The system of claim 1, further comprising a translation mechanism operatively coupled to the catheter and configured to facilitate translation of the cable of the catheter relative to the patient.

8. A position sensing system for an intravascular catheter comprising:
   a first friction wheel having a first surface, a second surface generally opposite the first surface, and a circumferential edge extending between the first and second surfaces;
   a second friction wheel positioned generally opposite the first friction wheel such that a cable of the intravascular catheter extends between the first friction wheel and the second friction wheel;
   a spring mechanism biased to press the first friction wheel and/or the second friction wheel against the cable of the intravascular catheter;
   a disc coaxially aligned with the first friction wheel, the disc configured to rotate with the first friction wheel and in a same direction as the first friction wheel, the disc having a radius larger than a radius of the first friction wheel;
   a first plurality of detectable areas disposed about a circumference of the disc, wherein each of the first plurality of detectable areas have a distinguishable magnetic strength or magnetic direction from every other detectable area of the first plurality of detectable areas; and
   at least one detector positioned proximate the disc, the at least one detector configured to generate a first position signal in response to directly detecting the distinguishable magnetic strength or magnetic direction of a first detectable area of the first plurality of detectable areas passing by the at least one detector and based on previously directly detecting the distinguishable magnetic strength or magnetic direction of a second detectable area of the first plurality of detectable areas, the first plurality of detectable areas configured to move relative to the at least one detector in response to rotation of the disc and the first friction wheel,
   wherein the second friction wheel includes a second plurality of detectable areas configured to move in response to rotation of the second friction wheel, the at least one detector being configured to generate a second position signal based on movement of the second plurality of detectable areas relative to the at least one detector, and
   wherein a direction of motion of the cable of the intravascular catheter is determined based on the first position signal and the second position signal that correspond to the detectable areas of the first plurality of detectable areas being detected at different times relative to detection of the second plurality of detectable areas.

9. The position sensing system of claim 8, wherein the spring mechanism is operatively coupled to the second friction wheel, and is configured to bias the second friction wheel toward the first friction wheel.

10. The position sensing system of claim 8, further comprising an intravascular processing engine configured to receive the first position signal and the second position signal, each being indicative of a position of the cable of the intravascular catheter.

11. The position sensing system of claim 10, wherein the processing engine is further configured to (i) receive secondary information from an intravascular sensor and (ii) combine the received secondary information with position information corresponding to a relative position at which the secondary information was acquired.

12. The position sensing system of claim 8, wherein the first friction wheel comprises a high-friction material about its circumferential edge.

13. The position sensing system of claim 8, further comprising a housing enclosing the first friction wheel, the second friction wheel, the spring mechanism, the disc, and the at least one detector.

14. A position sensing assembly for an intravascular system comprising:
   a housing that includes a groove for receiving an anchor portion of a catheter;
   a first friction wheel coupled to the housing;
   a disc coaxially aligned with the first friction wheel, the disc configured to rotate with the first friction wheel and in a same direction as the first friction wheel, the disc having a radius larger than a radius of the first friction wheel;
   a first position sensor coupled to the housing and including a first plurality of detectable elements and a first reference element, the first plurality of detectable elements being disposed about a circumference of the disc, wherein each of the first plurality of detectable elements have a distinguishable magnetic strength or magnetic direction from every other detectable element of the first plurality of detectable elements, the first position sensor configured to generate a first position signal based on the first reference element directly detecting the distinguishable magnetic strength or magnetic direction of a first detectable element of the first plurality of detectable elements passing by the first reference element and based on previously directly detecting the distinguishable magnetic strength or magnetic direction of a second detectable element of the first plurality of detectable elements, the first plurality of detectable elements configured to move relative to the first reference element in response to rotation of the disc and the first friction wheel;
   a second friction wheel coupled to the housing and operatively coupled to a bias spring, and
   a second position sensor including a second plurality of detectable elements and being configured to generate a second position signal, the second friction wheel including the second plurality of detectable elements,
   wherein the first and second friction wheels are positioned relative to the groove so that when the groove receives the anchor portion of the catheter, a catheter cable extends between the first and second friction wheels, and wherein the bias spring causes the second friction wheel to press against the cable when the cable extends between the first and second friction wheels, and wherein a direction of motion of the cable of the catheter is determined based on the first position signal and the second position signal that correspond to the detectable elements of the first plurality of detectable elements being detected at different times relative to detection of the second plurality of detectable elements.

15. The system of claim 1, wherein the first position sensor is configured to generate the first position signal by being configured to:
   identify an order in which the first reference element detects the first detectable element and the second detectable element;
   determine a linear distance and a direction travelled for the catheter based on the order in which the first reference element detects the first detectable element and the second detectable element; and
   generate the first position signal to indicate the linear distance and the direction travelled for the catheter.

16. The system of claim 1, wherein the second position sensor is configured to generate the second position signal based on a relationship between the first reference element and at least one detectable element of the second plurality of detectable elements.

17. The system of claim 1, wherein the second position sensor further includes a second reference element, the second position sensor being configured to generate the second position signal based on a relationship between the second reference element and at least one detectable element of the second plurality of detectable elements.

18. The position sensing system of claim 8, wherein the at least one detector comprises (i) a first detector positioned proximate the disc and configured to generate the first position signal and (ii) a second detector positioned proximate the second friction wheel and configured to generate the second position signal.

* * * * *